(12) United States Patent
Perry et al.

(10) Patent No.: US 8,932,231 B2
(45) Date of Patent: Jan. 13, 2015

(54) LACRIMAL DRAINAGE MANOMETER AND METHOD OF USE

(71) Applicant: The Cleveland Clinic Foundation, Cleveland, OH (US)

(72) Inventors: Julian D. Perry, Pepper Pike, OH (US); Craig D. Lewis, Fairview Park, OH (US); Ryan S. Klatte, Fairview Park, OH (US); Barry D. Kuban, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/828,732

(22) Filed: Mar. 14, 2013

(65) Prior Publication Data

US 2013/0204165 A1    Aug. 8, 2013

Related U.S. Application Data

(63) Continuation-in-part of application No. 13/234,242, filed on Sep. 16, 2011, now Pat. No. 8,460,230.

(60) Provisional application No. 61/383,372, filed on Sep. 16, 2010.

(51) Int. Cl.
*A61B 5/00* (2006.01)
*A61B 3/10* (2006.01)
(Continued)

(52) U.S. Cl.
CPC . *A61B 3/101* (2013.01); *A61B 3/16* (2013.01); *A61M 5/16886* (2013.01); *A61F 9/007* (2013.01); *G01F 1/34* (2013.01); *A61B 10/0045* (2013.01); *A61M 5/3137* (2013.01);
(Continued)

(58) Field of Classification Search
USPC ............. 600/486, 561; 604/21, 65, 187
See application file for complete search history.

(56) References Cited

U.S. PATENT DOCUMENTS

| | | |
|---|---|---|
| 5,795,307 A | 8/1998 | Krueger |
| 5,855,559 A | 1/1999 | Van Tassel et al. |

(Continued)

FOREIGN PATENT DOCUMENTS

WO    2012037428 A2    3/2012

OTHER PUBLICATIONS

PCT International Search Report and Written Opinion for PCT/US2011/051872, mailed Apr. 23, 2012, pp. 1-9.
(Continued)

*Primary Examiner* — Nicholas Lucchesi
*Assistant Examiner* — Gerald Landry, II
(74) *Attorney, Agent, or Firm* — Tarolli, Sundheim, Covell & Tummino LLP

(57) ABSTRACT

A lacrimal drainage manometer includes a syringe having a syringe body and a piston. The syringe body defines a fluid cavity in fluid communication with a cannula configured for insertion into at least a portion of a lacrimal drainage system. The piston dispenses a fluid from the fluid cavity through the cannula. A pressure sensor is operably coupled to the syringe for measuring fluid pressure in the fluid cavity. A position sensor operably coupled to the syringe measures the position of the piston relative to the syringe body. A user feedback unit in electrical communication with the pressure sensor and the position sensor provides user feedback based on data from at least one of the pressure sensor and the position sensor indicative of a condition of the lacrimal drainage system.

24 Claims, 18 Drawing Sheets

(51) Int. Cl.
    *A61B 3/16*     (2006.01)
    *A61M 5/168*     (2006.01)
    *A61F 9/007*     (2006.01)
    *G01F 1/34*     (2006.01)
    *A61B 10/00*     (2006.01)
    *A61M 5/31*     (2006.01)
    *A61M 5/315*     (2006.01)
    *A61M 5/32*     (2006.01)
    *A61M 5/48*     (2006.01)

(52) U.S. Cl.
    CPC .......... *A61M5/31511* (2013.01); *A61M 5/3293* (2013.01); *A61M 5/486* (2013.01); *A61M 2205/3334* (2013.01); *A61F 9/00772* (2013.01); *A61B 2010/0067* (2013.01)
    USPC .............................. 600/561; 604/21; 604/187

(56) References Cited

U.S. PATENT DOCUMENTS

| | | |
|---|---|---|
| 6,117,086 A | 9/2000 | Shulze |
| 6,428,502 B1 * | 8/2002 | Lang ................. 604/28 |
| 2002/0123716 A1 | 9/2002 | VanDiver et al. |
| 2004/0171983 A1 * | 9/2004 | Sparks et al. ................. 604/65 |
| 2005/0165363 A1 * | 7/2005 | Judson et al. ................. 604/209 |
| 2007/0060820 A1 | 3/2007 | Lofgren et al. |
| 2007/0112299 A1 * | 5/2007 | Smit et al. ................. 604/67 |
| 2008/0106859 A1 * | 5/2008 | Eguchi et al. ................. 361/681 |
| 2008/0114302 A1 * | 5/2008 | Neer ................. 604/154 |
| 2008/0255502 A1 * | 10/2008 | Jacobson et al. ................. 604/67 |
| 2009/0043253 A1 * | 2/2009 | Podaima ................. 604/67 |
| 2009/0270759 A1 * | 10/2009 | Wilson et al. ................. 600/561 |
| 2009/0326459 A1 * | 12/2009 | Shipway et al. ................. 604/155 |
| 2010/0274180 A1 * | 10/2010 | Donovan et al. ................. 604/65 |
| 2011/0060229 A1 * | 3/2011 | Hulvershorn et al. ........ 600/486 |
| 2011/0144530 A1 * | 6/2011 | Felder ................. 600/561 |
| 2011/0202012 A1 * | 8/2011 | Bartlett ................. 604/218 |
| 2011/0270131 A1 * | 11/2011 | Snow et al. ................. 600/587 |

OTHER PUBLICATIONS

PCT International Search Report and Written Opinion for PCT/US2014/019499, mailed May 30, 2014, pp. 1-16.

* cited by examiner

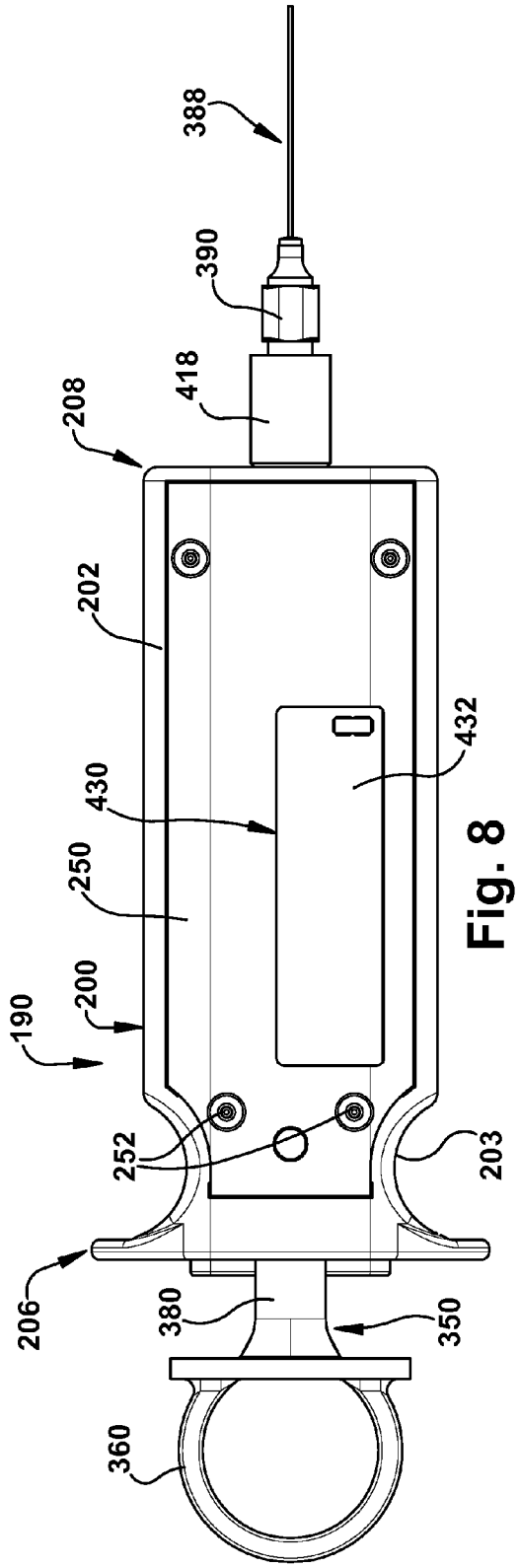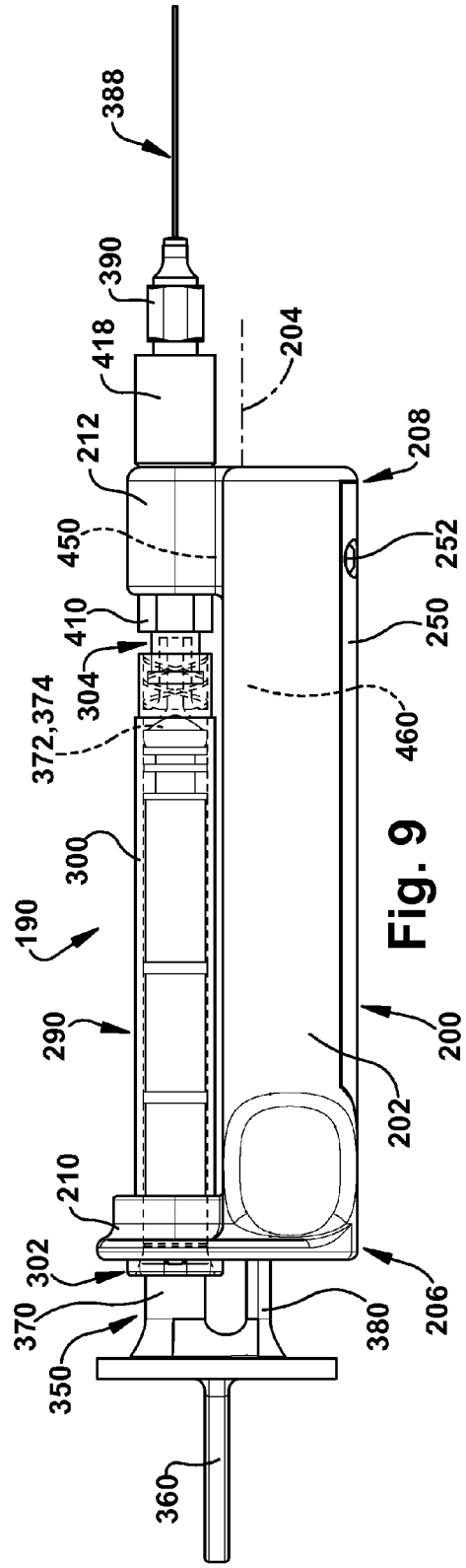

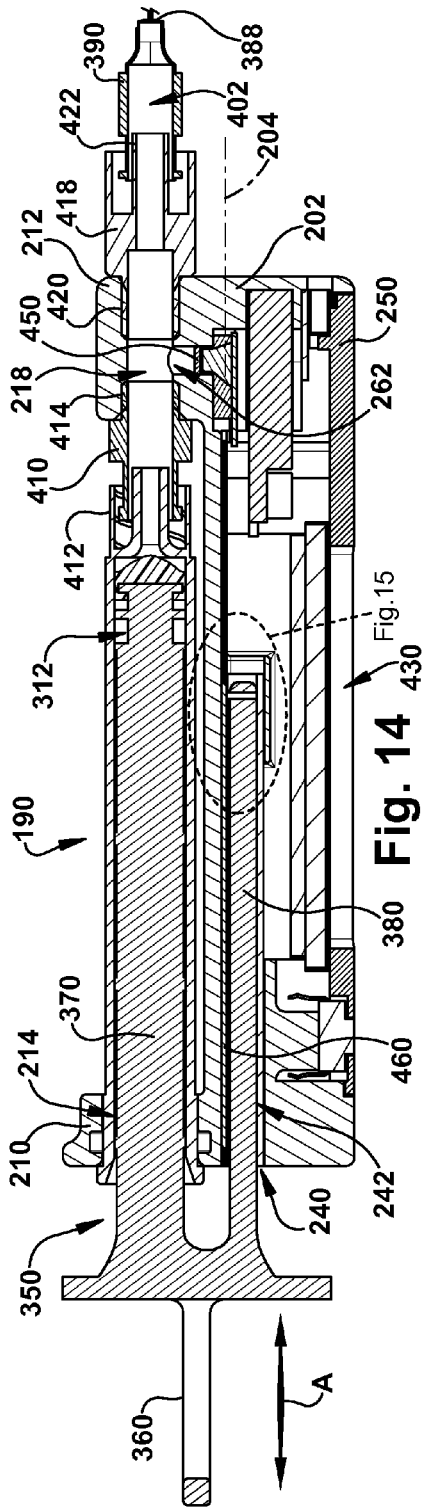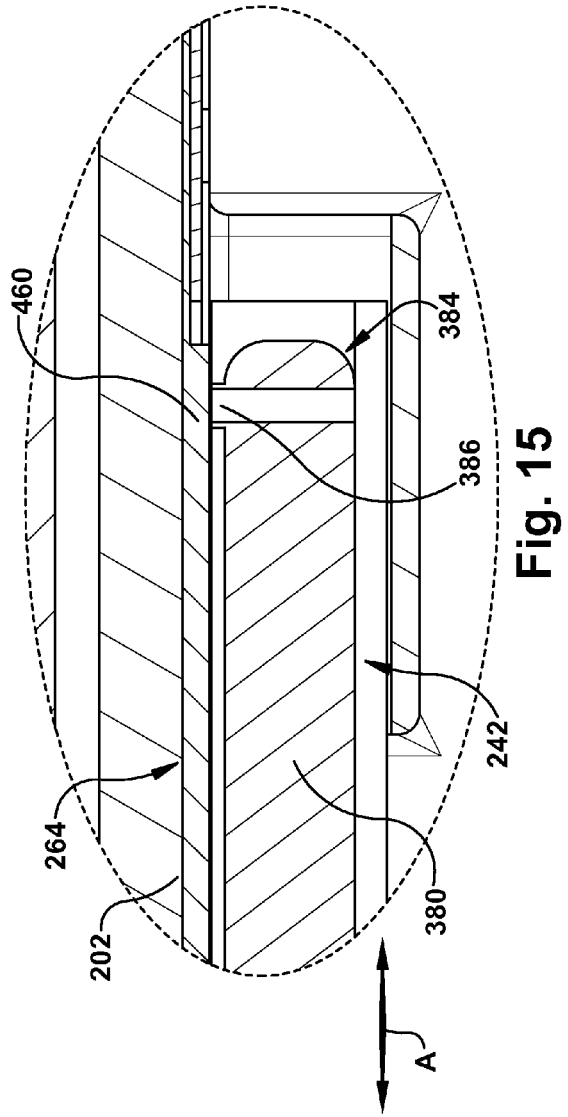

LACRIMAL DRAINAGE MANOMETER AND METHOD OF USE

RELATED APPLICATION

This application claims priority from U.S. patent application Ser. No. 13/234,242, filed Sep. 16, 2011, corresponding with U.S. Provisional Patent Application Ser. No. 61/383,372, filed Sep. 16, 2010, the subject matter of which is incorporated herein by reference.

TECHNICAL FIELD

The present invention relates generally to devices and methods for assessing the lacrimal drainage system, and more particularly to a lacrimal drainage manometer for determining at least one indicator of lacrimal drainage system function in a subject.

BACKGROUND OF THE INVENTION

Epiphora describes an overflow of tears caused by imperfect drainage of the tear-conducting passages. Epiphora is a common ophthalmic problem, accounting for 3% of ambulatory clinic visits. When tear shedding is extreme, it causes considerable annoyance for patients by degrading visual acuity. The cause of epiphora is usually benign; however, in some cases, malignant nasolacrimal duct obstruction occurs. Current office-based methods for assessing nasolacrimal duct obstruction provide only tactile feedback (i.e., a qualitative measure) for physicians to assess the patency of the nasolacrimal drainage system. Such methods are subjective and prone to overestimation and/or underestimation of lacrimal drainage pressure.

SUMMARY OF THE INVENTION

One aspect of the present invention includes a lacrimal drainage manometer having a syringe with a syringe body and a piston. The syringe body defines a fluid cavity in fluid communication with a cannula configured for insertion into at least a portion of a lacrimal drainage system. The piston dispenses a fluid from the fluid cavity through the cannula. A pressure sensor is operably coupled to the syringe for measuring fluid pressure in the fluid cavity. A position sensor operably coupled to the syringe measures the position of the piston relative to the syringe body. A user feedback unit in electrical communication with the pressure sensor and the position sensor provides user feedback based on data from at least one of the pressure sensor and the position sensor indicative of a condition of the lacrimal drainage system.

Another aspect of the present invention includes a method for accurately determining at least one indicator of lacrimal drainage system function during nasolacrimal irrigation. One step of the method includes providing a lacrimal drainage manometer comprising a syringe in fluid communication with a cannula, a pressure sensor operably coupled to the syringe for determining fluid pressure within the syringe, a position sensor operably coupled to the syringe for determining fluid flow rate through the syringe based upon the change in position of a portion of the syringe, and a user feedback unit in electrical communication with each of the pressure sensor and the position sensor. Next, a portion of the cannula is inserted into a portion of the lacrimal drainage system. At least one indicator of lacrimal drainage system function is then quantitatively detected during injection of a fluid through the cannula. The at least one indicator of lacrimal drainage system function includes at least one of lacrimal drainage pressure, fluid flow rate, or nasolacrimal resistance.

Another aspect of the present invention includes a method for determining the presence of an obstruction in a lacrimal drainage system. One step of the method includes providing a lacrimal drainage manometer comprising a syringe in fluid communication with a cannula, a pressure sensor operably coupled to the syringe for determining fluid pressure within the syringe, a position sensor operably coupled to the syringe for determining fluid flow rate through the syringe, and a user feedback unit in electrical communication with each of the pressure sensor and the position sensor. Next, a portion of the cannula is inserted into a portion of the lacrimal drainage system. At least one indicator of lacrimal drainage system function is then quantitatively detected during injection of a fluid through the cannula. The at least one indicator is at least one of lacrimal drainage pressure, fluid flow rate or nasolacrimal resistance. An increased or decreased level of the at least one indicator as compared to a control level is indicative of an obstruction.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 8 is a top view of the lacrimal drainage manometer of FIG. 7;

FIG. 9 is a side view of the lacrimal drainage manometer of FIG. 7;

FIG. 14 is a cross-sectional view of the lacrimal drainage manometer of FIG. 7;

FIG. 15 is an enlarged view of a portion of the lacrimal drainage manometer of FIG. 14;

DETAILED DESCRIPTION

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the context of the present invention, it will be understood that when an element, structure, or component is referred to as being "on," "attached" to, "connected" to, "coupled" with, "contacting," etc., another element, structure or component, it can be directly on, attached to, connected to, coupled with or contacting the other element or intervening elements may also be present. In contrast, when an element, structure or component is referred to as being, for example, "directly on," "directly attached" to, "directly connected" to, "directly coupled" with or "directly contacting" another element, there are no intervening elements, structures or components present. It will also be appreciated by those of skill in the art that references to a structure or feature that is disposed "adjacent" another feature may have portions that overlap or underlie the adjacent feature.

As used herein, the term "electrical communication" can include both wired and wireless communication between elements, structures or components of the present invention.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "lacrimal drainage system" can refer to the structures concerned with tear collection, such as the lacrimal lake, puncta, canaliculi, lacrimal sac, and nasolacrimal duct, as well as the structures described below.

Figure 1A:
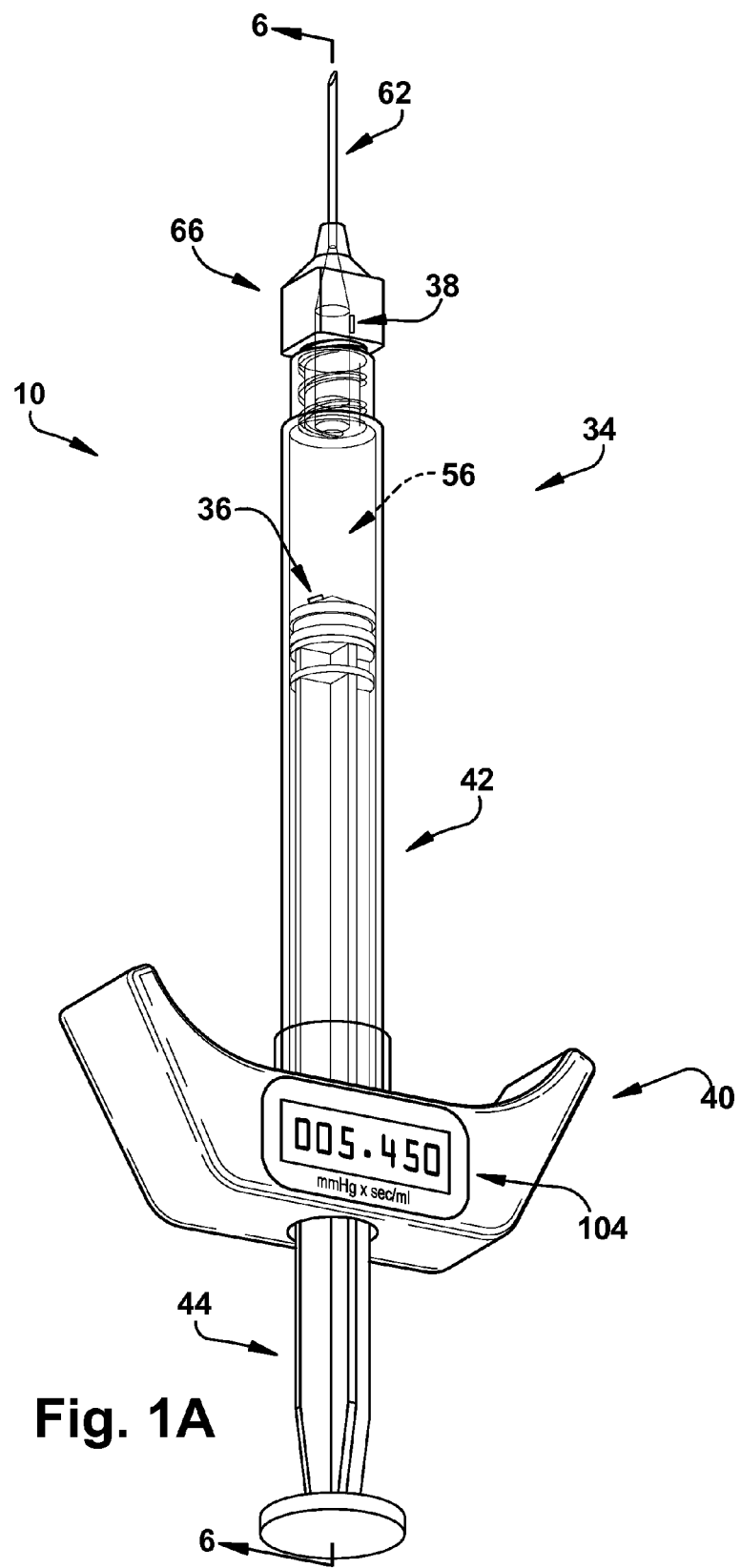
FIG. 1A is an assembled perspective view of a lacrimal drainage manometer comprising a syringe and a user feedback unit constructed in accordance with one aspect of the present invention.
Figure 1B:
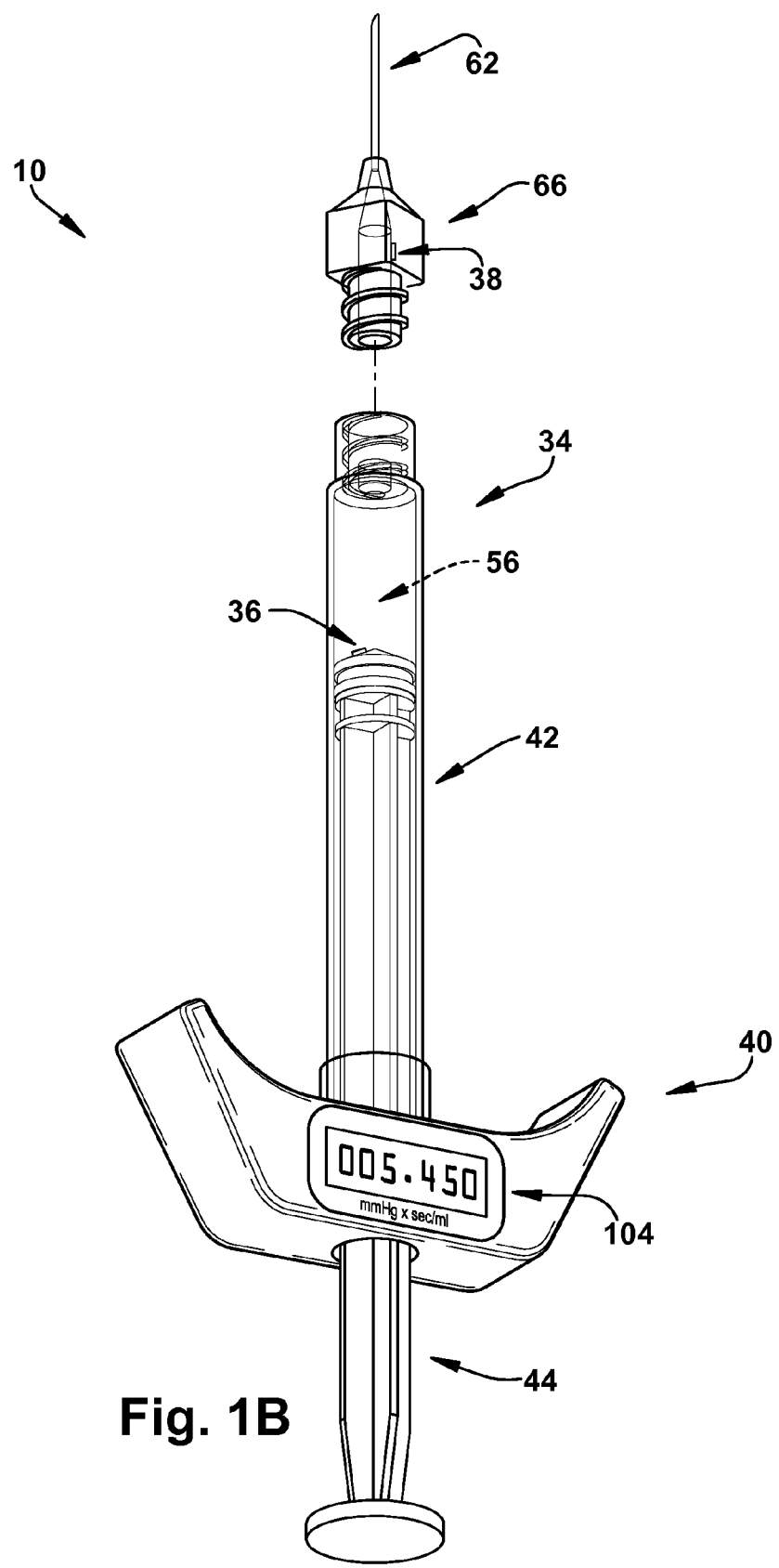
FIG. 1B is an exploded perspective view of the lacrimal drainage manometer in FIG. 1A.
Figure 2:
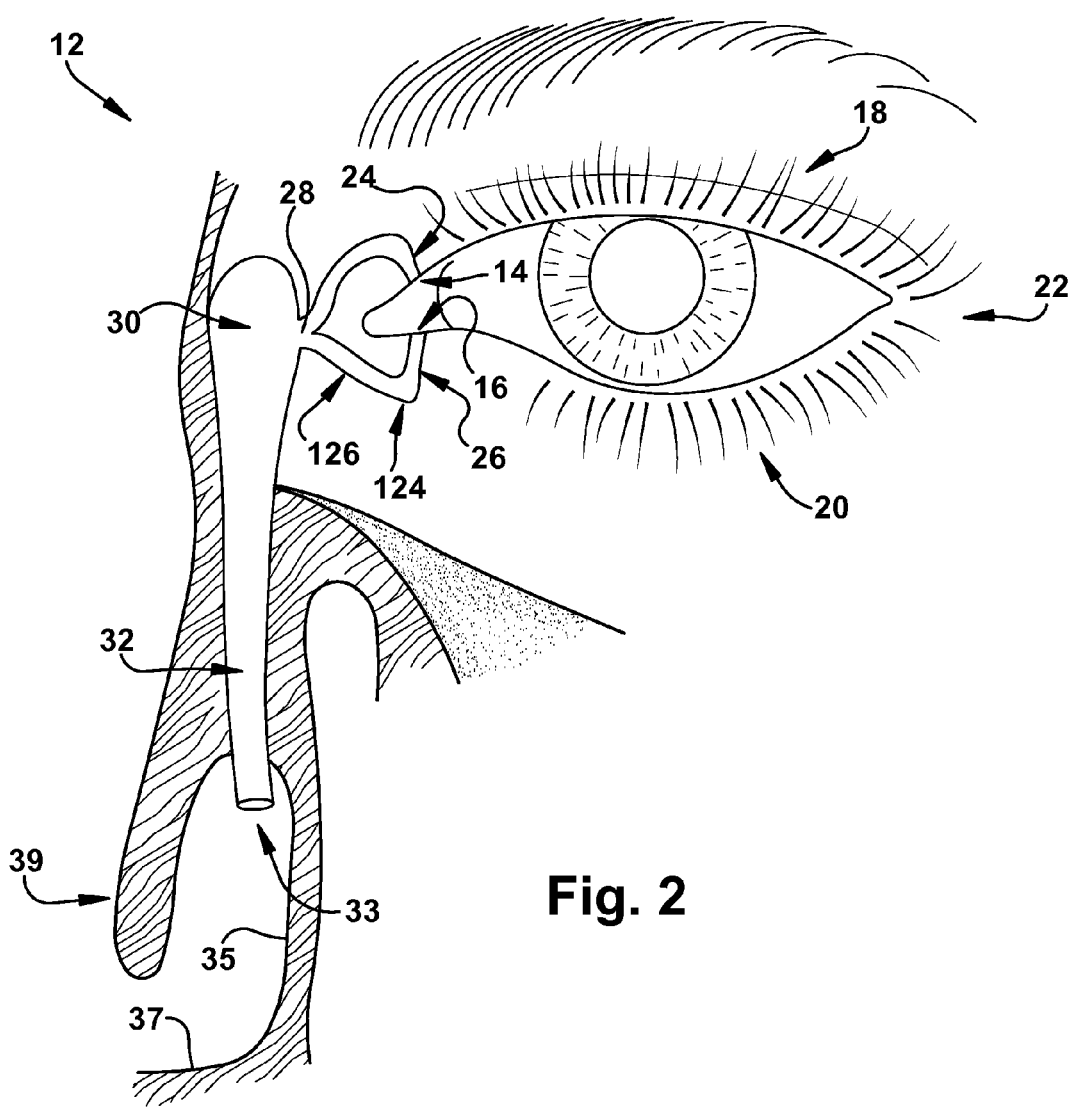
FIG. 2 is a cross-sectional frontal illustration of the lacrimal drainage system of a human subject.

The present invention relates generally to devices and methods for assessing the lacrimal drainage system, and more particularly to a lacrimal drainage manometer for determining at least one indicator of lacrimal drainage system function in a subject. As representative of one aspect of the present invention, FIGS. 1A-B illustrate a handheld lacrimal drainage manometer 10 that may be used, for example, for clinical assessment of suspected nasolacrimal duct obstruction. Unlike conventional approaches to assessing the lacrimal drainage system 12 (FIG. 2), which rely on tactile or qualitative feedback measures, the present invention advantageously provides a lacrimal drainage manometer 10 (FIGS. 1A-B) for quantitatively measuring at least one indicator of lacrimal drainage system function. As described in more detail below, the added quantitative measurements made possible by the present invention provide important clinical information that may be used to help guide the choice of intervention for subjects with a dysfunctional lacrimal drainage system 12 (e.g., epiphora).

A brief description of the relevant anatomy and physiology of the lacrimal drainage system 12 (FIG. 2) is provided to assist the reader with understanding the present invention. The orbital portion of the lacrimal gland (not shown) is located in the superotemporal orbit (not shown), and the palpebral portion of the lacrimal gland is located on the posterior surface (not shown) of the superotemporal upper lid (not shown). The lacrimal gland produces the aqueous portion of the tear film. Ductules (not shown) from the orbital portion of the lacrimal gland pass through the adjacent palpebral lacrimal gland to empty in the superior conjunctival cul-de-sac (not shown). Smaller accessory lacrimal glands in the upper and lower lids also contribute to tear production. The tears bathe the surface of the eye and then drain into the nose via the lacrimal drainage system 12.

The lacrimal drainage system 12 comprises a pair of small openings; namely, the superior punctum 14 and inferior punctum 16, which are located on the medial upper and lower lids 18 and 20 of the eye 22. Tears flow into these puncta 14 and 16, which lead to two small diameter delicate tubes; namely, the superior canaliculus 24 and the inferior canaliculus 26. The canaliculi 24 and 26 join together as a short common canaliculus 28 that enters into the larger lacrimal sac 30. The tears then flow from the lacrimal sac 30 down the nasolacrimal duct 32 and out an opening (not shown), which empties into the nose on the lateral nasal wall (not shown) and onto the nasal floor (not shown) beneath the inferior turbinate (not shown).

Referring to FIGS. 1A-B, the lacrimal drainage manometer 10 comprises a syringe 34, at least one pressure sensor 36 operably coupled to the syringe, at least one flow sensor 38 operably coupled to the syringe, and a user feedback unit 40. The syringe 34 includes a syringe body 42 and a piston 44. The syringe body 42 (FIGS. 3A-B) includes oppositely disposed first and second ends 46 and 48, an outer surface 50, and an inner surface 52. The inner surface 52 and the outer surface 50 define a syringe wall 54. The inner surface 52 of the syringe body 42 defines a fluid cavity 56 that extends between the first and second ends 46 and 48. The first end 46 includes an opening 58 for slidably receiving the piston 44. The second end 48 includes a hollow port 60 for flowing a fluid from the fluid cavity 56 into a cannula 62 (FIGS. 1A-B). The syringe body 42 can be made of any one or combination of known medical grade material(s), such as plastic (e.g., polyethylene).

Figure 3A:
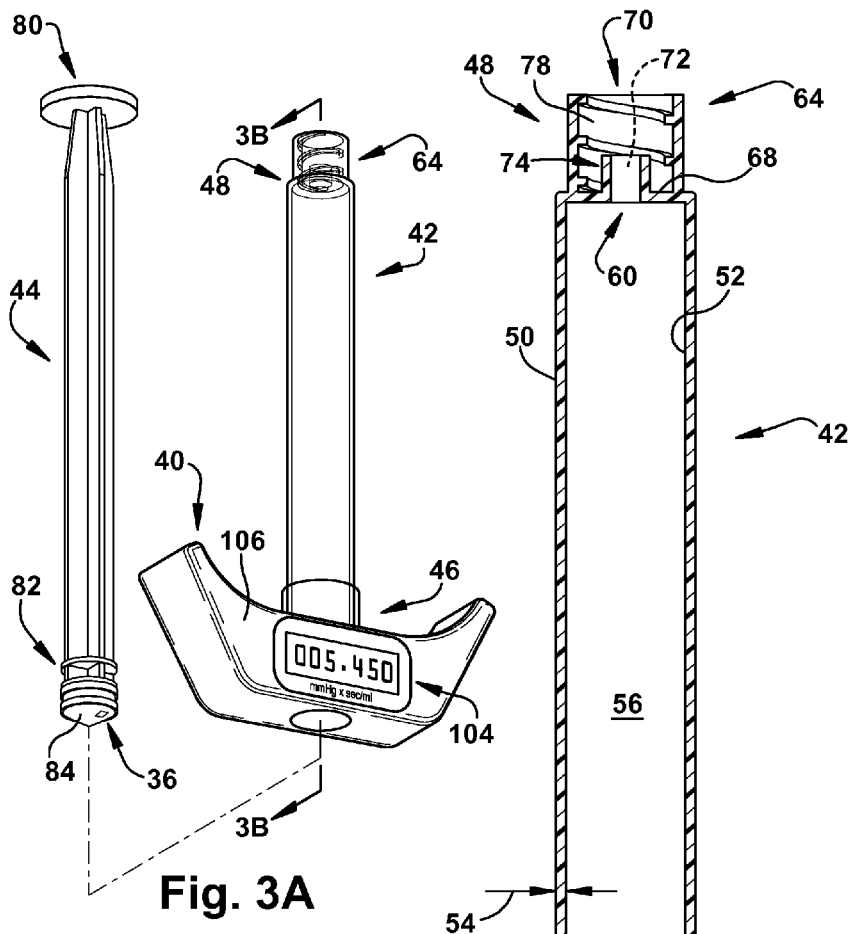
FIG. 3A is a perspective view showing a syringe body of the lacrimal drainage manometer shown in FIGS. 1A-B.
Figure 3B:
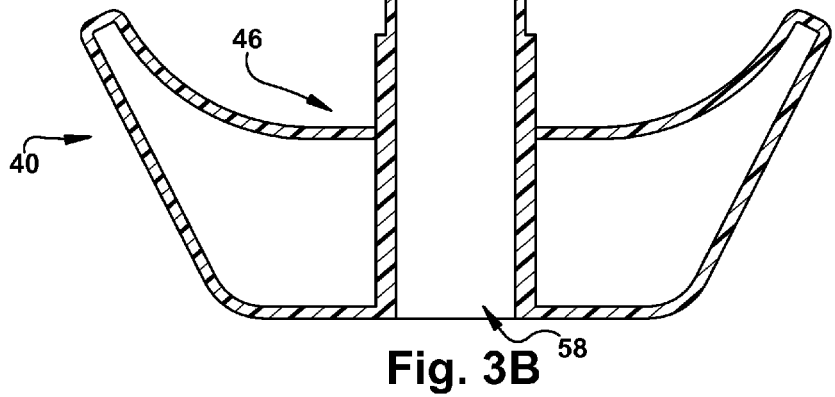
FIG. 3B is a cross-sectional view taken along Line 3B-3B in FIG. 3A.

The second end 48 of the syringe body 42 includes a docking portion 64 configured to releasably mate with a portion of a detachable member 66. As shown in FIGS. 3A-B, the docking portion 64 includes a cavity (not shown in detail) defined by the inner surface 52 of the syringe body 42, an upper surface 68, and a second opening 70, which is configured to receive a portion of the detachable member 66. The hollow port 60 extends from the upper surface 68 into the cavity. The port 60 includes a lumen 72 that is in communication with the fluid cavity 56. A distal end 74 of the port 60 is configured to mate with a lumen 76 (FIG. 5A) of the detachable member 66. The inner surface 52 (FIGS. 3A-B) of the docking portion 64 includes one or more grooves 78 for mating with a portion of the detachable member 66. As shown in FIGS. 3A-B, the groove(s) 64 can be configured in a spiral pattern about the inner surface 52 of the docking portion 64.

The piston 44 (FIG. 3A) is configured to be slidably placed within the fluid cavity 56. The piston 44 has a rod-shaped configuration and includes a handle portion 80 and a distal tip 82. The distal tip 82 includes a distal surface 84 for contacting a fluid and forming a fluid-tight seal with the inner surface 52 of the syringe body 42. The distal tip 82 can be comprised of a flexible or semi-flexible water-proof or water-resistant material, such as rubber. The distal tip 82 is configured so that no pressure can escape from a fluid side of the piston 44 to an atmospheric side of the piston. The piston 44 can be slidably placed in the fluid cavity 56 to cause a fluid (e.g., saline) to be withdrawn or expelled through the cannula 62. All or only a portion of the piston 44 can be can be made of any one or combination of known medical grade material(s), such as plastic.

Figures 4, 5A:
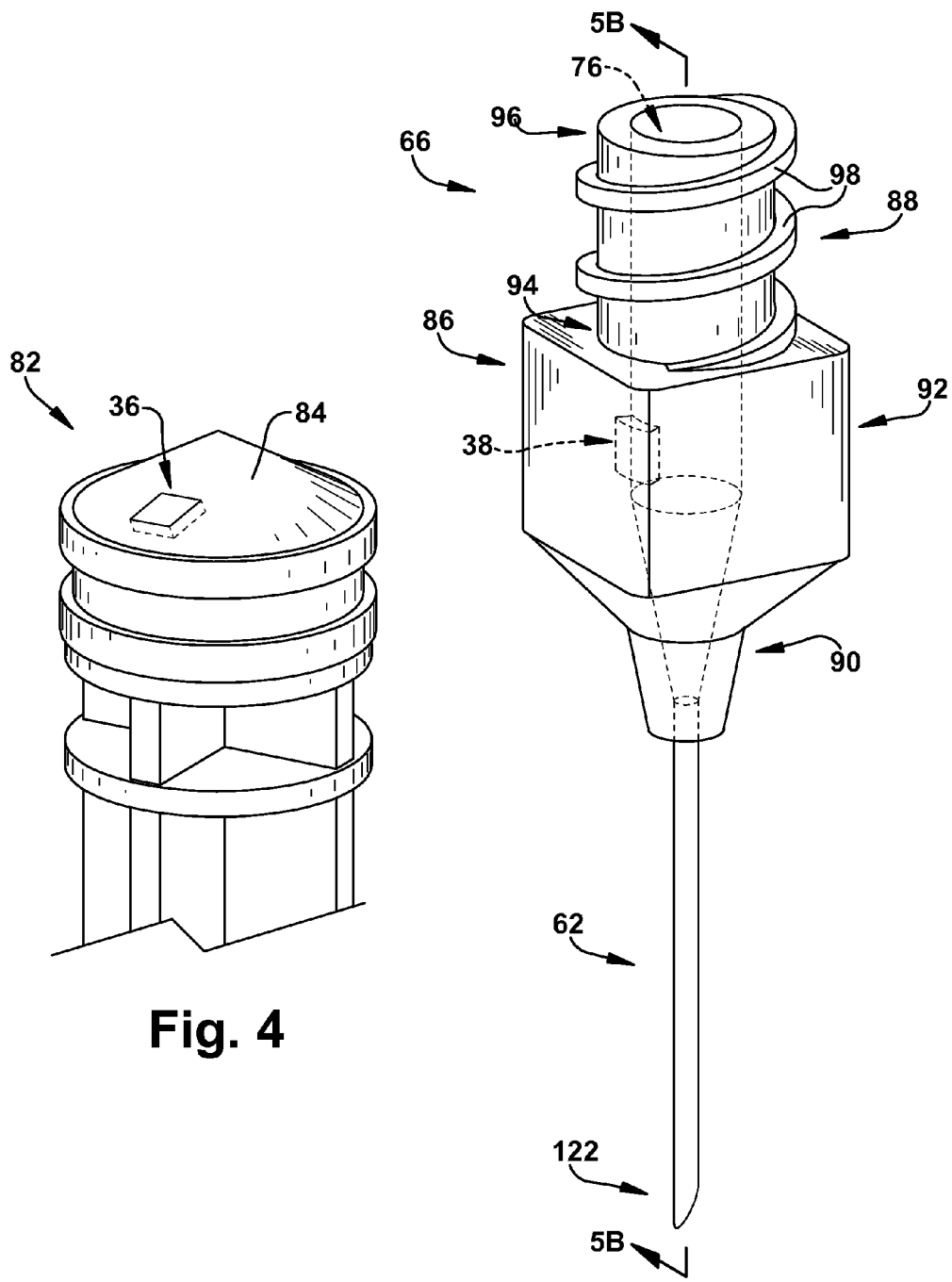
FIG. 4 is a magnified perspective view showing a distal end of a piston comprising the syringe in FIGS. 1A-B.
FIG. 5A is a perspective view showing a detachable member of the syringe in FIGS. 1A-B.

The lacrimal drainage manometer 10 (FIGS. 1A-B) includes a plurality of sensors for determining at least one fluid flow characteristic of a fluid that is injected through the syringe 34 into the lacrimal drainage system 12. As shown in FIG. 3A, the lacrimal drainage manometer 10 includes at least one pressure sensor 36 that is operably coupled to the syringe 34. For example, a pressure sensor 36 can be attached (e.g., directly attached) to the inner surface 52 of the syringe body 42. Alternatively, a pressure sensor 36 can be integrated into a portion of the wall 54 comprising the syringe body 42. In one example of the present invention, a pressure sensor 36 can operate within a general dynamic pressure range and with a sensing area that is sufficiently small to be mounted to the distal surface 84 of the piston 44 (FIG. 4). Various alternative placements of a pressure sensor 36 (or sensors) will be readily apparent to those skilled in the art.

The pressure sensor 36 measures the pressure being applied to fluid in the fluid cavity 56, and is configured to provide a signal representative of fluid pressure inside the fluid cavity. The pressure sensor 36 is in electrical communication with a circuit (not shown) and/or software (not shown) to provide a user with feedback (e.g., pressure values) via the user feedback unit 40. For instance, the pressure sensor 36 can communicate (e.g., wirelessly) with a digital signal processing circuit (not shown) that is incorporated into the user feedback unit 40. Examples of pressure sensors 36 suitable for use as part of the lacrimal drainage manometer 10 are known in the art and can include, for example, MEMS-based pressure sensors.

Figures 5B, 5C:
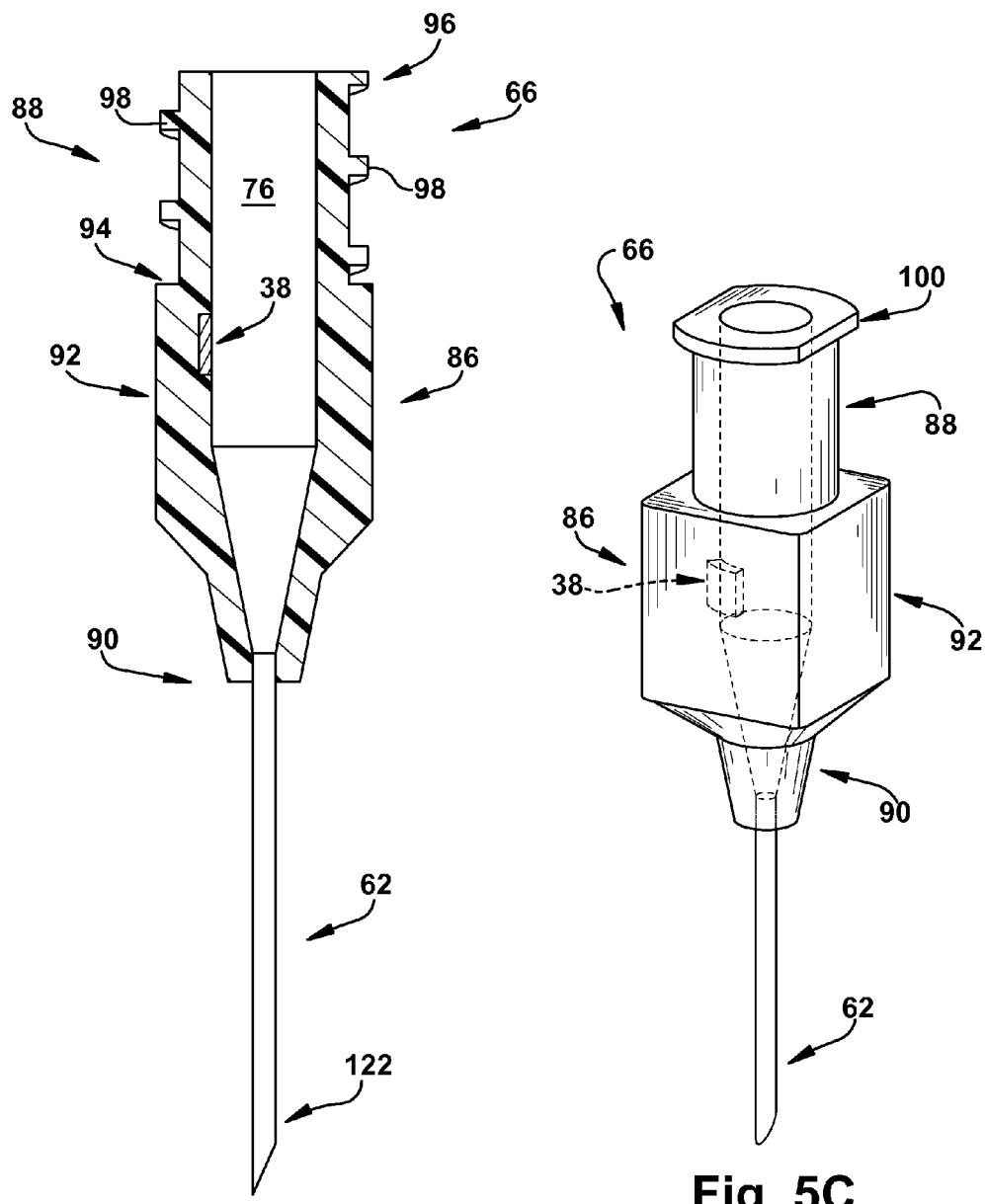
FIG. 5B is a cross-sectional view taken along Line 5B-5B in FIG. 5A.
FIG. 5C is a perspective view showing an alternative configuration of the detachable member in FIG. 5A.

As shown in FIGS. 5A-B, the lacrimal drainage manometer 10 further includes a detachable member 66 configured to releasably mate with the docking portion 64 of the syringe body 42. The detachable member 66 includes a main body portion 86 that is integrally formed with the cannula 62. The main body portion 86 further includes an intermediate portion 92 that extends between first and second ends 88 and 90. The intermediate portion 92 has a cubic configuration to facilitate grasping during attachment of the detachable member 66 to the docking portion 64. It will be appreciated that the intermediate portion 92 can have any other shape or configuration to facilitate ease of attachment to the docking portion 64. For example, the intermediate portion 92 can have a rounded or cylindrical configuration (not shown) and optionally include a tacky surface to facilitate grasping. The detachable member 66 can be made of a medical grade material (e.g., plastic), and can be opaque, semi-opaque, or transparent.

Figure 6:
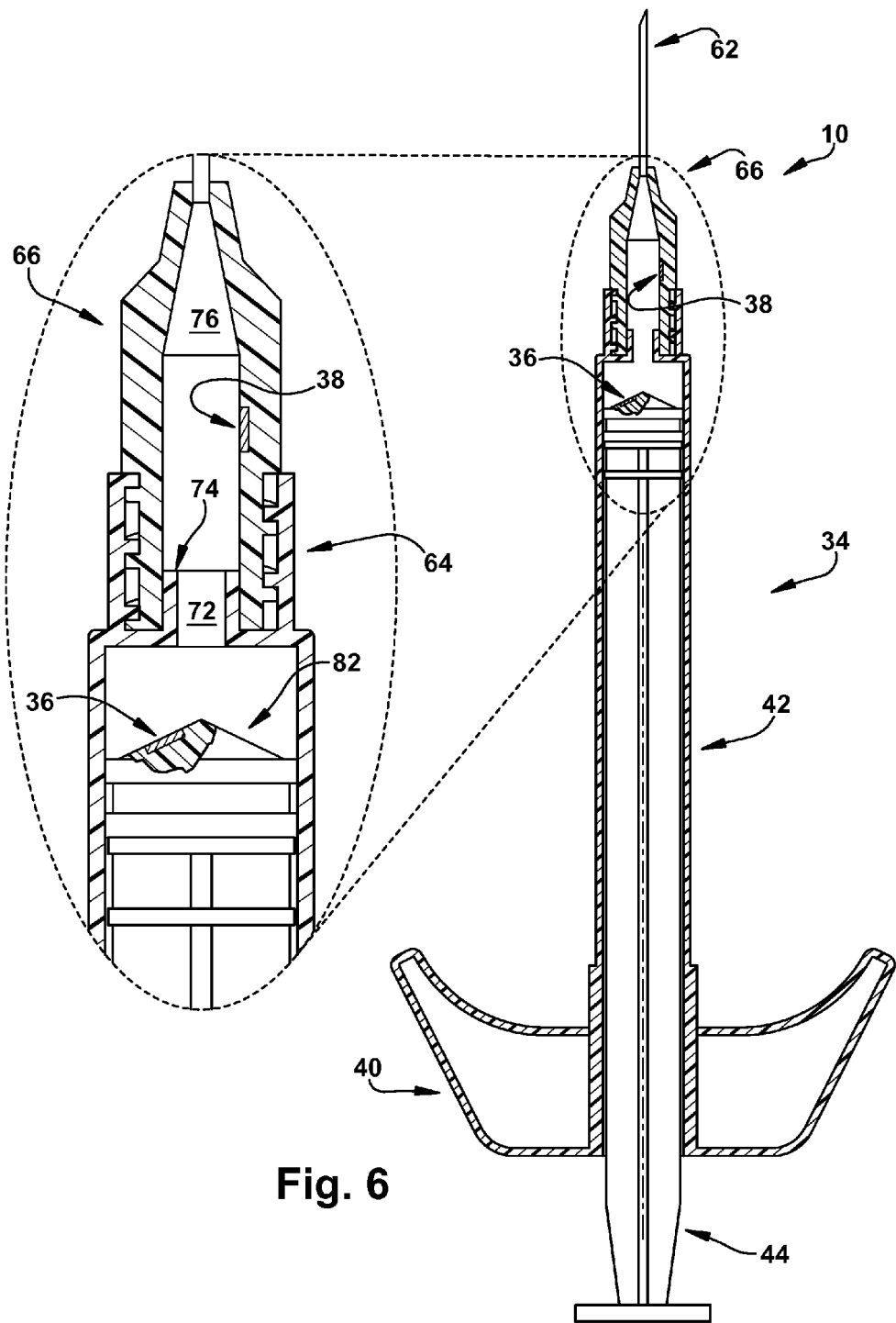
FIG. 6 is a cross-sectional view taken along Line 6-6 in FIG. 1A.

A lumen 76 (FIG. 5B) extends between the first and second ends 88 and 90 of the detachable member 66. The first end 88 is configured to mate with the docking portion 64 of the syringe body 42 such that the lumen 76 and the fluid cavity 56 are in communication with one another (FIG. 6). The first end 88 has a cylindrical configuration and includes oppositely disposed proximal and distal ends 94 and 96. The proximal end 94 is directly attached to the intermediate portion 92. The first end 88 includes a spiral-shaped lip or edge 98 that extends between the proximal and distal ends 96 and 98. The edge 98 is configured to mate with the groove(s) 78 of the docking portion 64 (e.g., by applying torque to the detachable member 66 and/or the syringe body 42). It will be appreciated that the first end 88 of the detachable member 66 and the docking portion 64 of the syringe body 42 can have other configurations, such as a single peripheral edge 100 (FIG. 5C) configured to mate with the groove(s) 78.

The second end 90 of the main body portion 86 has a tapered configuration and is integrally formed with the cannula 62. The tapered configuration of the second end 90 can reduce the profile of the syringe 34 so that the cannula 62 can be more easily visualized during use of the lacrimal drainage manometer 10.

The cannula 62 is configured for insertion into at least a portion of the lacrimal drainage system 12. For example, the cannula 62 can be dimensioned so that a portion of the cannula forms a substantially tight seal when inserted into the lacrimal drainage system 12. The dimensions of the cannula 62 can vary based on the subject's anatomy, the condition being assessed, the procedure being performed, etc. Illustrative cannula sizes can range from 27-gauge to 19-gauge.

The lacrimal drainage manometer 10 includes at least one flow sensor 38 that is operably coupled to the syringe 34. For example, the detachable member 66 can include at least one flow sensor 38 that is operably coupled thereto. As shown in FIGS. 5A-B, a flow sensor 38 can be attached (e.g., directly attached) to the lumen 76 of the detachable member 66. For example, the flow sensor 38 can be integrated into a portion of the wall defining the lumen 76. Alternatively, the flow sensor 38 can be directly attached to the wall that defines the lumen 76. Various alternative placements of the flow sensor 38 (or sensors) will be readily apparent to those skilled in the art.

The flow sensor 38 measures the flow rate of fluid passing through the syringe 34 (e.g., the lumen 76 of the detachable member 66). The flow sensor 38 is configured to provide a signal representative of fluid flow to the user feedback unit 40. The flow sensor 38 is in electrical communication with a circuit (not shown) and/or software (not shown) to provide a user with feedback (e.g., flow value(s)) via the user feedback unit 40. For instance, the flow sensor 38 can communicate (e.g., wirelessly) with a digital signal processing circuit (not shown) that is incorporated into the user feedback unit 40. Examples of flow sensors 38 suitable for use as part of the lacrimal drainage manometer 10 are known in the art and can include, for example, MEMS-based flow sensors.

Referring again to FIGS. 1A-B, the lacrimal drainage manometer 10 additionally comprises a user feedback unit 40 configured to provide user feedback based on data from a pressure sensor 36 and/or a flow sensor 38. The user feedback unit 40 comprises an ergonomically-shaped housing 102. For example, the housing 102 can have a wing-shaped configuration to facilitate ease of handling of the lacrimal drainage manometer 10 (e.g., by a physician). The housing 102 can be releasably, snugly, slidably or frictionally fit about the syringe body 42. For example, the housing 102 can be attached (e.g., directly attached) to the first end 46 of the syringe body 42. The housing 102 can also include a lumen (not shown in detail) configured to allow the piston 44 to be inserted into the fluid cavity 56.

The housing 102 can be compact and cover only a portion of the syringe body 42, thereby allowing a user visual contact with fluid in the fluid cavity 56. The housing 102 can be multi-use while the syringe 34 can be single-use or disposable. The housing 102 can be configured as a lightweight, balanced structure that does not provide eccentric weight or unbalance or unduly affect the injection operation of the lacrimal drainage manometer 10.

The housing 102 includes an integrated display 104 configured to provide an analog, digital, graphical and/or aural indication of sensor data. For example, the display 104 can comprise a screen disposed on, or integrated into, a first side 106 of the housing 102. The display 104 can be configured to provide a user with substantially real-time sensor data (e.g., pressure, flow rate and/or nasolacrimal resistance) during operation of the lacrimal drainage manometer 10. As shown in FIGS. 1A-B, the display 104 can provide a visible readable output of pressure (e.g., 5 mmHg) and flow rate (e.g., 400 sec/ml). It will be appreciated that the display 104 can also include additional features, such as an alarm that audibly or visibly indicates when a safety threshold (e.g., application of excessive pressure during injection) is at risk of being breached during operation of the lacrimal drainage manometer 10.

The user feedback unit 40 can include a power supply (not shown) and/or power saving unit (not shown). The power supply can include a small, high performance battery (not shown) with suitable shape and dimensions for fitting into the housing 102. The power supply and/or power saving unit can include a mechanism for cutting and restoring power in order to save power when the lacrimal drainage manometer 10 is not in use. For example, the power saving unit can cut power when a finger rest (not shown) of the housing 102 has not been pressed for a certain amount of time. The power unit can restore power when the finger rest is pressed.

The user feedback unit 40 is in electrical communication with each of the pressure sensor(s) 36 and the flow sensor(s) 38. For example, the user feedback unit 40 can include a digital processor circuit (not shown) that can be in electrical communication with each of the pressure sensor(s) 36 and the flow sensor(s) 38. The digital processor circuit can be held in the housing 102. The digital processor circuit can communicate (e.g., wirelessly) with the pressure sensor(s) 36 and/or the flow sensor(s) 38 to obtain desired sensor data. The wireless communication between electronic components of the present invention can be carried out, for example, using BLUETOOTH transmission configuration or any other suitable digital communication protocol or configuration.

The user feedback unit 40 can include hardware and/or software configured to:

read a signal from a pressure sensor 36 representative of the fluid pressure in the syringe 34;

convert the signal representative of fluid pressure in the syringe to a pressure value representative of the fluid pressure;

read a signal from a flow sensor 38 representative of the fluid flow rate through the syringe;

convert the signal representative of fluid flow in the syringe to a flow value representative of the fluid flow;

calculate an experienced nasolacrimal resistance to the expelled fluid flow as the quotient between the pressure and the fluid flow; and present the resistance value, the pressure, and/or the flow rate on the display 104.

As noted above, the software and/or hardware of the user feedback unit 40 is configured to calculate a resistance experienced by the syringe 34 when expelling its contents. For example, nasolacrimal resistance can be calculated from flow and pressure data by the aid of the Poiseuille-Hagen equation, or other fluid mechanics equations, which have been incorporated into the software of the user feedback unit 40. The results are visualized on the display 104, and the user can use them to make a decision on further actions.

Figure 7:
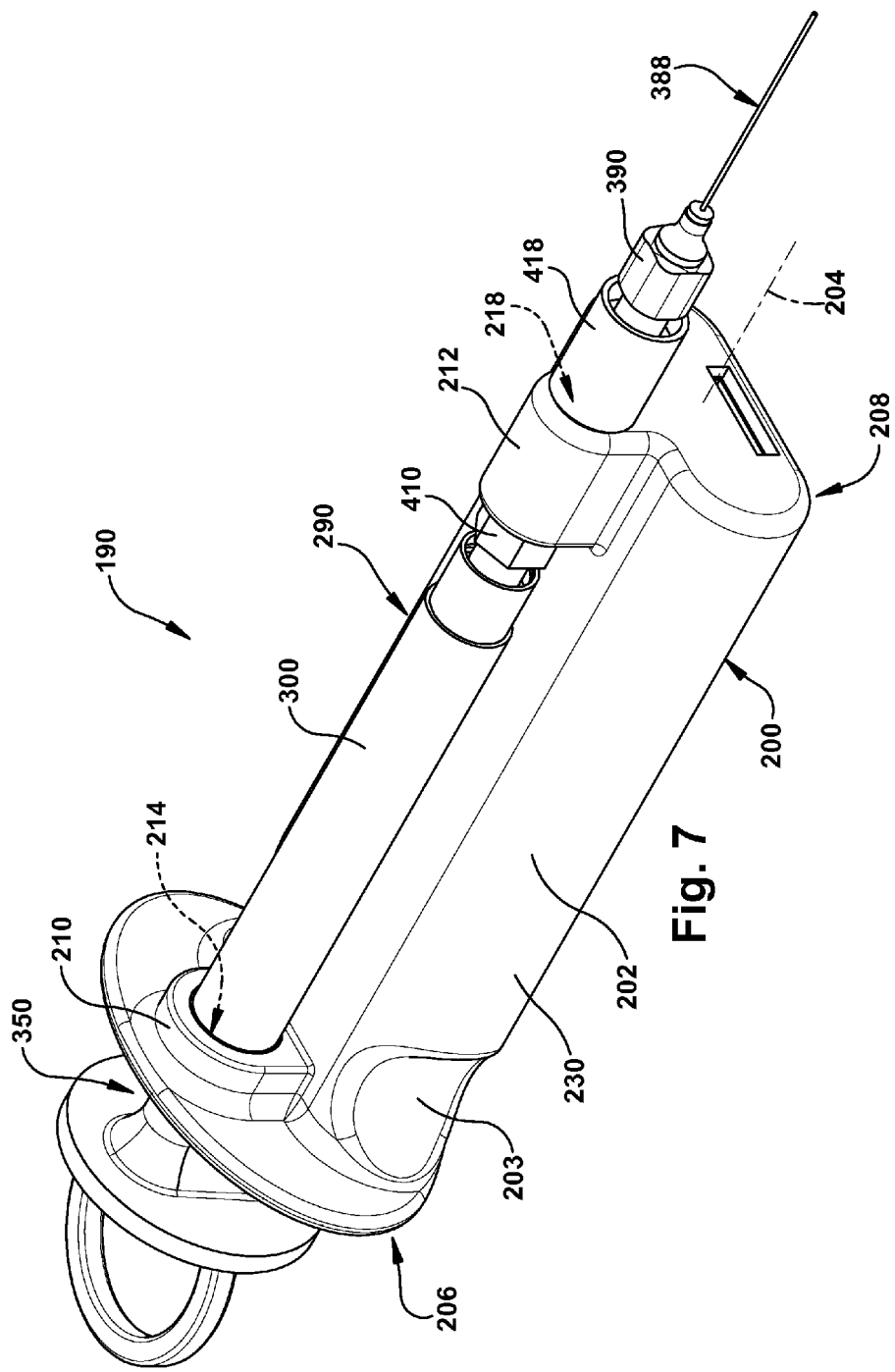
FIG. 7 is an assembled perspective view of a lacrimal drainage manometer in accordance with another aspect of the present invention.

FIGS. 7-16 illustrate a lacrimal drainage manometer 190 in accordance with another aspect of the present invention. Referring to FIGS. 7-9, the lacrimal drainage manometer 190 includes a housing 200, a syringe 290, at least one pressure sensor 450 operably coupled to the syringe, at least one position sensor 460 operably coupled to the syringe, and a user feedback unit 430. First and second fittings 410, 418 mechanically and fluidly connect the syringe 290 to the housing 200.

The housing 200 can be multi-use while the syringe 290 can be single-use or disposable. The housing 200 can be configured as a lightweight, balanced structure that does not provide eccentric weight or unbalance or unduly affect the injection operation of the lacrimal drainage manometer 190.

Figure 11:
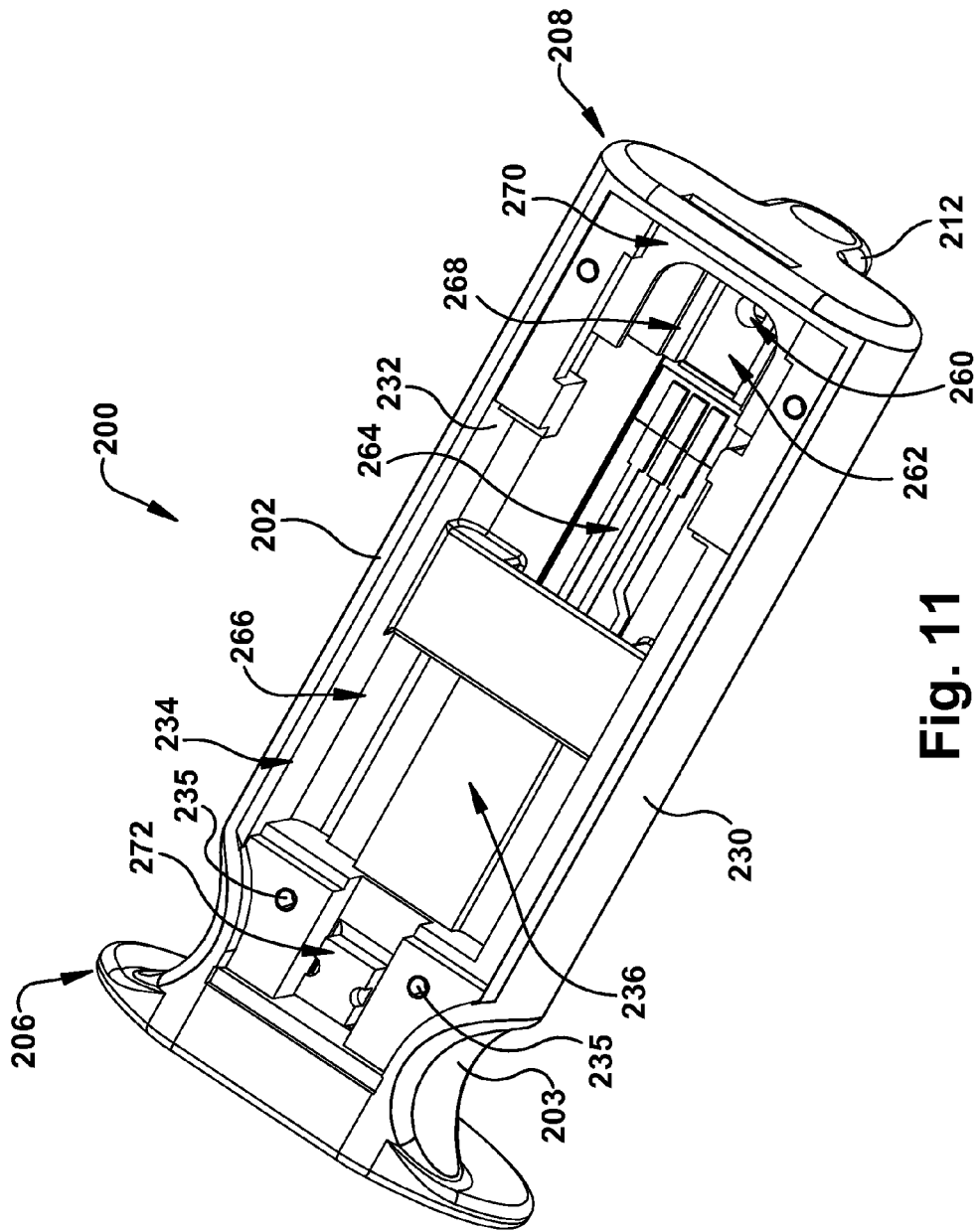
FIG. 11 is a perspective view of the housing of the lacrimal drainage manometer of FIG. 7.

Referring to FIGS. 7 and 11, the housing 200 includes a generally rectangular main body 202 that extends generally along a centerline 204 from a first end 206 to a second end 208. The body 202 includes an outer surface 230 and an inner surface 232. Indentations 203 formed into the outer surface 230 of the first end 206 of the housing 200 facilitate grasping and handling of the housing. A blind opening 234 extends from the outer surface 230 and cooperates with the inner surface 232 to define an interior space 236 of the body 202. The opening 234 is closed by a cover 250 with a series of fasteners 252 secured to threaded openings 235 in the body 202 (see FIG. 8).

A pair of projections 210, 212 extends away from the outer surface 230 and generally away from the centerline 204. Each projection 210, 212 includes a substantially circular passage 214 and 218, respectively, that extends entirely though the projection. The passages 214, 218 extend generally parallel to the centerline 204 and are coaxial with one another.

A series of recesses 262-272 is formed into the inner surface 232 within the interior space 236 for receiving a plurality of electrical components associated with the user feedback unit 430. Furthermore, an additional passage 260 extends from the inner surface 232 and away from the interior space 236 entirely through the main body 202 to a position generally between the projections 210, 212.

Figure 10:
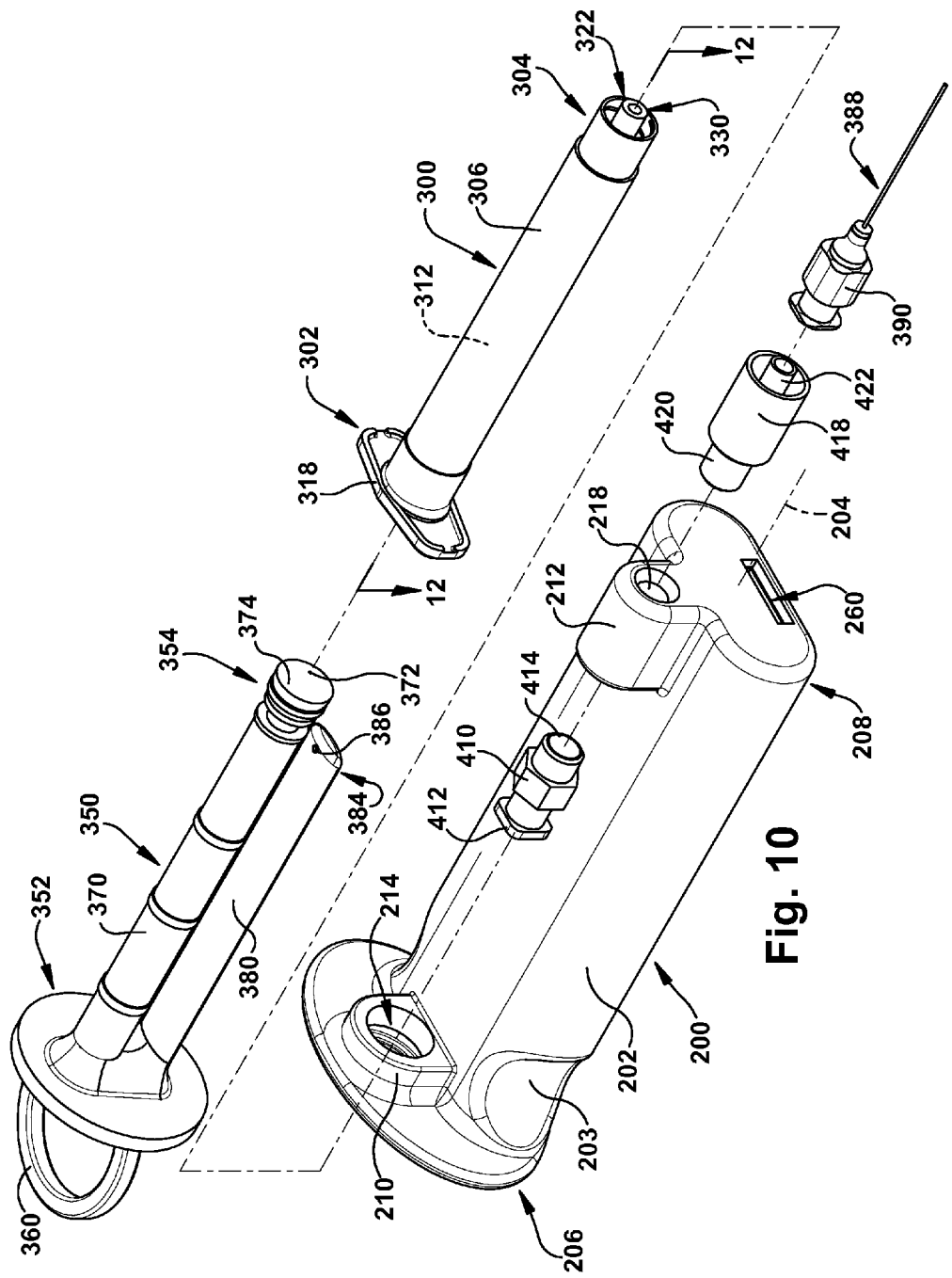
FIG. 10 is an exploded perspective view of the lacrimal drainage manometer of FIG. 7.
Figure 12:
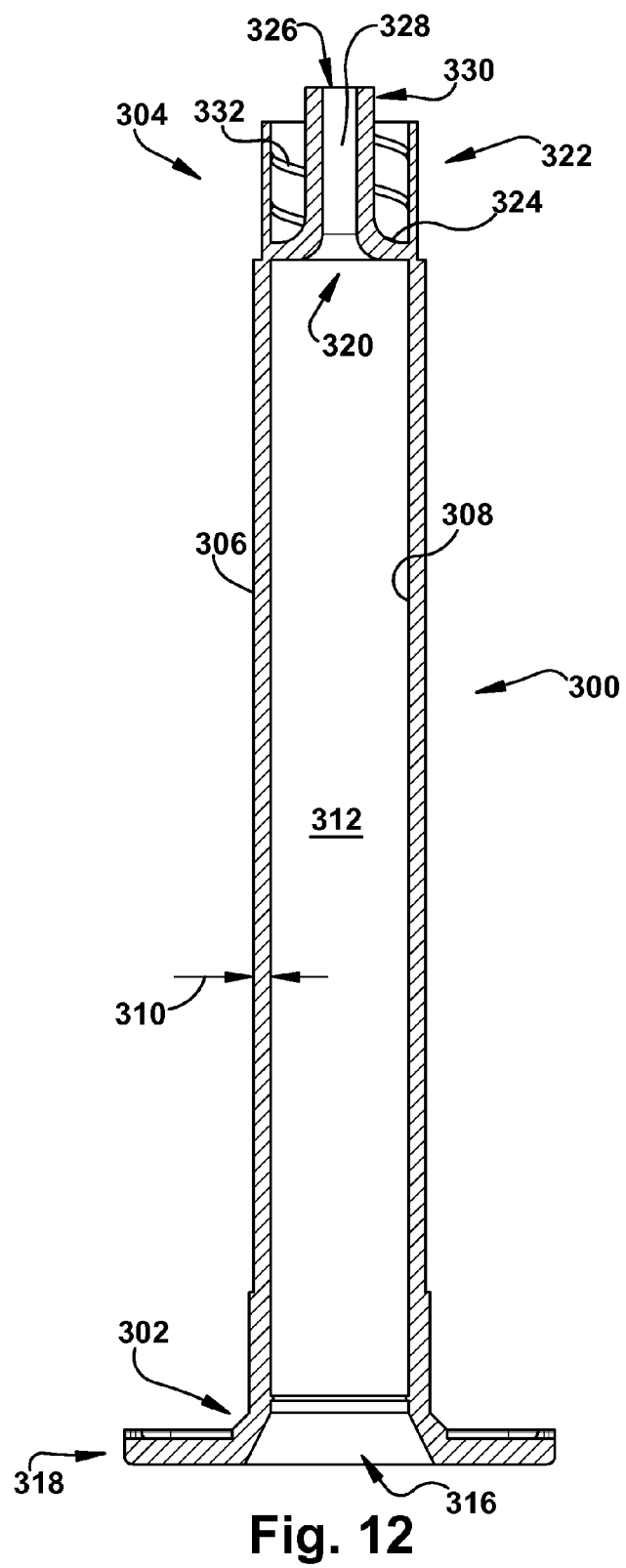
FIG. 12 is a cross-sectional view of a syringe body of the lacrimal drainage manometer of FIG. 7 taken along Line 12-12 of FIG. 10.

Referring to FIGS. 10 and 12, the syringe 290 includes a syringe body 300 and a piston member 350. The syringe body 300 includes oppositely disposed first and second ends 302 and 304, an outer surface 306, and an inner surface 308. The inner surface 308 and the outer surface 306 cooperate to define a syringe wall 310. The inner surface 308 defines a fluid cavity 312 that extends between the first and second ends 302 and 304 (i.e., entirely through the syringe body 300). The first end 302 includes a radially extending flange 318 and an opening 316 for slidably receiving a portion of the piston member 350. The second end 304 includes a hollow port 320 for flowing a fluid from the fluid cavity 312 into a cannula 388 (see FIG. 7). The syringe body 300 can be made of any one or combination of known medical grade material(s), such as plastic (e.g., polyethylene) and may be opaque, semi-opaque, or transparent such that the presence or amount of fluid within the fluid cavity 312 may be readily visible to the user.

The second end 304 of the syringe body 300 includes a docking portion 322 that includes a cavity (not shown in detail) defined by the inner surface 308 of the syringe body 300, an upper surface 324, and an opening 326. The hollow port 320 extends from the upper surface 324 into the cavity and terminates at a distal end 330. The port 320 includes a lumen 328 in fluid communication with the fluid cavity 312.

The distal end 330 of the docking portion 322 includes one or more grooves 332. As shown in FIG. 10, the groove(s) 332 can be configured in a spiral pattern about the inner surface 308 of the docking portion 322, although other configurations are contemplated.

Referring to FIG. 7, the syringe body 300 is inserted into the projection 210 in the first end 206 of the body 202 until the flange 318 abuts the projection and the second end 304 of the syringe body is positioned near the projection 212 at the second end 208 of the housing. The projections 210, 212 on the housing 200 can be compact and cover only a portion of the syringe body 300, thereby allowing a user visual contact with fluid in the fluid cavity 312.

Referring to FIG. 10, the first fitting 410 fluidly and mechanically connects the syringe body 300 to the housing 200. In particular, the first fitting 410 has a first end 412 configured to mate with the distal end 330 of the port 320. More specifically, the first end 412 of the first fitting 410 mates with the groove(s) 332 at the distal end 330. The first fitting 410 has a second end 414 forming a luer-lock with the passage 218 of the projection 212 on the housing 200. The first fitting 410 provides fluid communication between the lumen 312 of the syringe body 300 and the passage 218.

The piston member 350 has a generally longitudinal shape and extends from a first end 352 to a second end 354. The piston member 350 is configured to be slidably placed within both the fluid cavity 312 of the syringe body 300 and the interior space 236 of the housing 200. In particular, the piston member 350 includes a piston 370 configured to slide within the fluid cavity 312, and a plunger arm 380 configured to slide within the interior space 236 of the housing 200. A handle portion 360 connects the piston 370 to the plunger arm 380 at the first end 360 of the piston member 350.

The piston 370 has a rod-shaped configuration and extends away from the handle portion 360 towards the second end 354 of the piston member 350, terminating at a distal tip 372. The distal tip 372 includes a distal surface 374 for contacting a fluid and forming a fluid-tight seal with the inner surface 308 of the syringe body 300. The distal tip 372 can be comprised of a flexible or semi-flexible water-proof or water-resistant material, such as rubber. The distal tip 372 is configured so that no pressure can escape from a fluid side of the piston 370 to an atmospheric side of the piston. The piston 370 can be slidably placed in the fluid cavity 312 to cause a fluid (e.g., saline) to be withdrawn or expelled through the cannula 388. All or only a portion of the piston 370 can be can be made of any one or combination of known medical grade material(s), such as plastic.

The plunger arm 380 extends away from the handle portion 360 towards the second end 354 of the piston member 350 and parallel to the piston 370. The plunger arm 380 may have a substantially elliptical cross-section and terminates at a distal end 384 on which a pin or projection 386 is secured or formed integrally therewith. The pin 386 extends from the distal end 384 of the plunger arm 380 towards the piston 370 but does not engage or abut the piston. The plunger arm 380 is slidably received in the interior space 236 of the housing 200 via an opening 240 in the first end 206 of the main body 202 (see FIG. 14).

The distal end 384 of the plunger arm 380 is inserted through the opening 240 into a passage 242 in the housing 200 to place the pin 386 within the interior space 236 of the housing 200. Due to this construction and the configuration of the piston member 350, movement of the syringe 290 in the direction indicated by the arrow "A" in FIG. 14 causes the pin 386 to move within the interior space 236 along the length of the housing. The direction A is generally along or parallel to the centerline 204 of the housing 200. Since the piston 370 and plunger arm 380 are connected together via the handle portion 360, moving the handle in the direction generally indicated by "A" along or parallel to the centerline 204 causes simultaneous movement of the piston 370 within the fluid cavity 312 of the syringe body 300 and of the pin 386 within the interior space 236 of the housing 200.

Figure 13:
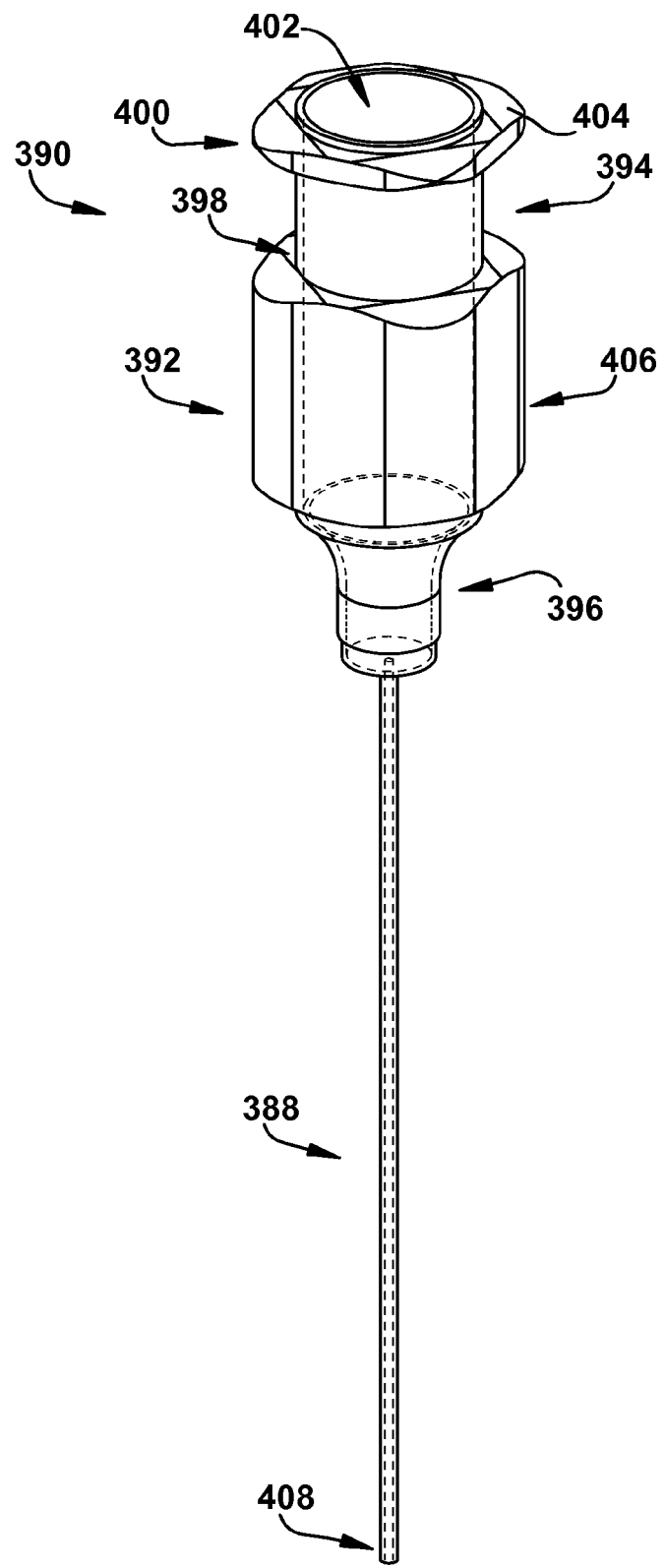
FIG. 13 is perspective view of a detachable member of the lacrimal drainage manometer of FIG. 7.

As shown in FIG. 13, the detachable member 390 includes a main body portion 392 integrally formed with the cannula 388. The main body portion 392 includes an intermediate portion 406 that extends between first and second ends 394 and 396. The detachable member 390 can be made of a medical grade material (e.g., plastic), and can be opaque, semi-opaque, or transparent. A lumen 402 extends between the first and second ends 394 and 396 of the detachable member 390. The first end 394 has a cylindrical configuration and includes oppositely disposed proximal and distal ends 398 and 400. The proximal end 398 is directly attached to the intermediate portion 406. The distal end 400 includes a radially extending spiral-shaped lip or edge 404.

The second end 396 of the main body portion 392 has a tapered configuration and is integrally formed with the cannula 388. The tapered configuration of the second end 396 can reduce the profile of the syringe 290 so that the cannula 388 can be more easily visualized during use of the lacrimal drainage manometer 290.

The cannula 388 is configured for insertion into at least a portion of the lacrimal drainage system 12. For example, the cannula 388 can be dimensioned so that a portion of the cannula forms a substantially tight seal when inserted into the lacrimal drainage system 12. The dimensions of the cannula 388 can vary based on the subject's anatomy, the condition being assessed, the procedure being performed, etc. Illustrative cannula 388 sizes can range from 27-gauge to 19-gauge.

Referring to FIG. 10, the second fitting 418 fluidly and mechanically connects the detachable member 390 to the housing 200. In particular, the second fitting 418 provides fluid communication between the lumen 402 of the detachable member 390 and the passage 218. The second fitting 418 has a first end 420 forming a luer-lock with the passage 218 of the projection 212 on the housing 200. The second fitting 418 has a second end 422 configured to mate with the first end 394 of the detachable member 390. More specifically, the second end 422 of the second fitting 420 is received by the lumen 402 of the detachable member 390. It will be appreciated that the first end 394 of the detachable member 390 and the second fitting 420 can have other mating configurations (e.g., a threaded connection).

The intermediate portion 406 of the detachable member 390 has a cubic configuration to facilitate grasping during attachment of the detachable member 390 to the second fitting 420. It will be appreciated that the intermediate portion 406 can have any other shape or configuration to facilitate ease of attachment to the second fitting 420. For example, the intermediate portion 406 can have a rounded or cylindrical configuration (not shown) and optionally include a tacky surface to facilitate grasping.

In any case, since each fitting 410, 420 places the syringe body 300 and the detachable member 390, respectively, in fluid communication with the passage 218, the fittings likewise cooperate to place the cavity 312 of the syringe body in fluid communication with the lumen 402 of the detachable member.

The lacrimal drainage manometer 190 further includes a plurality of sensors for determining at least one fluid flow characteristic of a fluid that is injected through the syringe 290 into the lacrimal drainage system 12. As shown in FIG.

14, the lacrimal drainage manometer 190 includes at least one pressure sensor 450 that is operably coupled to the syringe 290. The pressure sensor 450 can be mounted in a first recess 262 in the housing 200 (see also FIG. 11). Due to the connection between the syringe 290 and the housing 200 via the fittings 410, 418 the first recess 262 is in fluid communication with the fluid cavity 312 of the syringe body 300. Alternatively, the pressure sensor 450 can be attached (e.g., directly attached) to the inner surface 308 of the syringe body 300 or integrated into a portion of the wall 310 of the syringe body (not shown). In another example of the present invention, the pressure sensor 450 can operate within a general dynamic pressure range and with a sensing area that is sufficiently small to be mounted to the distal surface 374 of the piston 370. Various alternative placements of a pressure sensor 450 will be readily apparent to those skilled in the art.

The pressure sensor 450 measures the pressure being applied to fluid in the fluid cavity 312 and is configured to provide a signal representative of fluid pressure inside the fluid cavity. The pressure sensor 450 is in electrical communication with a circuit (not shown) and/or software (not shown) to provide a user with feedback (e.g., pressure values) via the user feedback unit 430. For instance, the pressure sensor 450 can communicate (e.g., wirelessly) with a digital signal processing circuit (not shown) that is incorporated into the user feedback unit 430. Examples of pressure sensors 450 suitable for use as part of the lacrimal drainage manometer 190 are known in the art and can include, for example, MEMS-based pressure sensors.

The lacrimal drainage manometer 190 also includes at least one position sensor 460 operably coupled to the syringe 290. In one instance, the position sensor 460 constitutes a linear resistor capable of detecting the change in position of an object in close proximity to the position sensor. The position change may be expressed or calculated as a change in absolute position along the position sensor 460 or a change in relative position along the position sensor. The position sensor 460 extends generally along or parallel to the centerline 204 of the housing 200 and is positioned within the second recess 264 in the housing (see FIGS. 11 and 15). The position sensor 460 is aligned generally with the opening 240 in the housing 200 such that movement of the plunger arm 380 and, in particular, movement of the pin 386 in the direction A can be monitored by the position sensor. Various alternative placements of the position sensor 460 will be readily apparent to those skilled in the art.

The position sensor 460 is used to determine the flow rate of fluid passing through the syringe 290 (e.g., through the lumen 402 of the detachable member 390) by monitoring the change in longitudinal position of the plunger arm 380. More specifically, the position sensor 460 is configured to provide a signal representative of the change in longitudinal position of the plunger arm 380 relative to the housing 200, which is ultimately used to calculate the flow rate through the syringe 290.

In use, and referring to FIGS. 14 and 15, the position sensor 460 senses the change in position of the pin 386 along the length of the position sensor as the plunger arm 380 moves in the direction A upon movement of the handle portion 360 in the direction A. The plunger arm 380 and piston 370 move as a single unit due to mutual connection with the handle portion 360 and, thus, sensing the change in position of the plunger arm in the interior space 236 necessarily senses the change in position of the piston 370 within the syringe body 300. The change in position of the pin 386 can be input into the following formula to determine the flow rate through the syringe 290:

$$\text{Flow rate} = \Delta x \cdot A_s / \Delta t$$

where x is the change in position of the pin 386 along the position sensor 460, $A_s$ is the cross-sectional area of the piston 370 (substantially constant), and $\Delta t$ is the change in time.

Although the present invention is illustrated as using a separate plunger arm 380 and pin 386 thereon to indirectly monitor the position of the piston 370, it will be appreciated that the position sensor 460 may be positioned and configured to directly monitor the position of the piston such that the plunger arm is unnecessary. Accordingly, the position sensor 460 may directly or indirectly measure the position and change in position of the piston 370 relative to the syringe body 300 in accordance with the present invention.

The position sensor 460 is in electrical communication with a circuit (not shown) and/or software (not shown) to provide a user with feedback (e.g., flow value(s)) via the user feedback unit 430. For instance, the position sensor 460 can communicate (e.g., wirelessly) with a digital signal processing circuit (not shown) that is incorporated into the user feedback unit 430.

Figure 16:
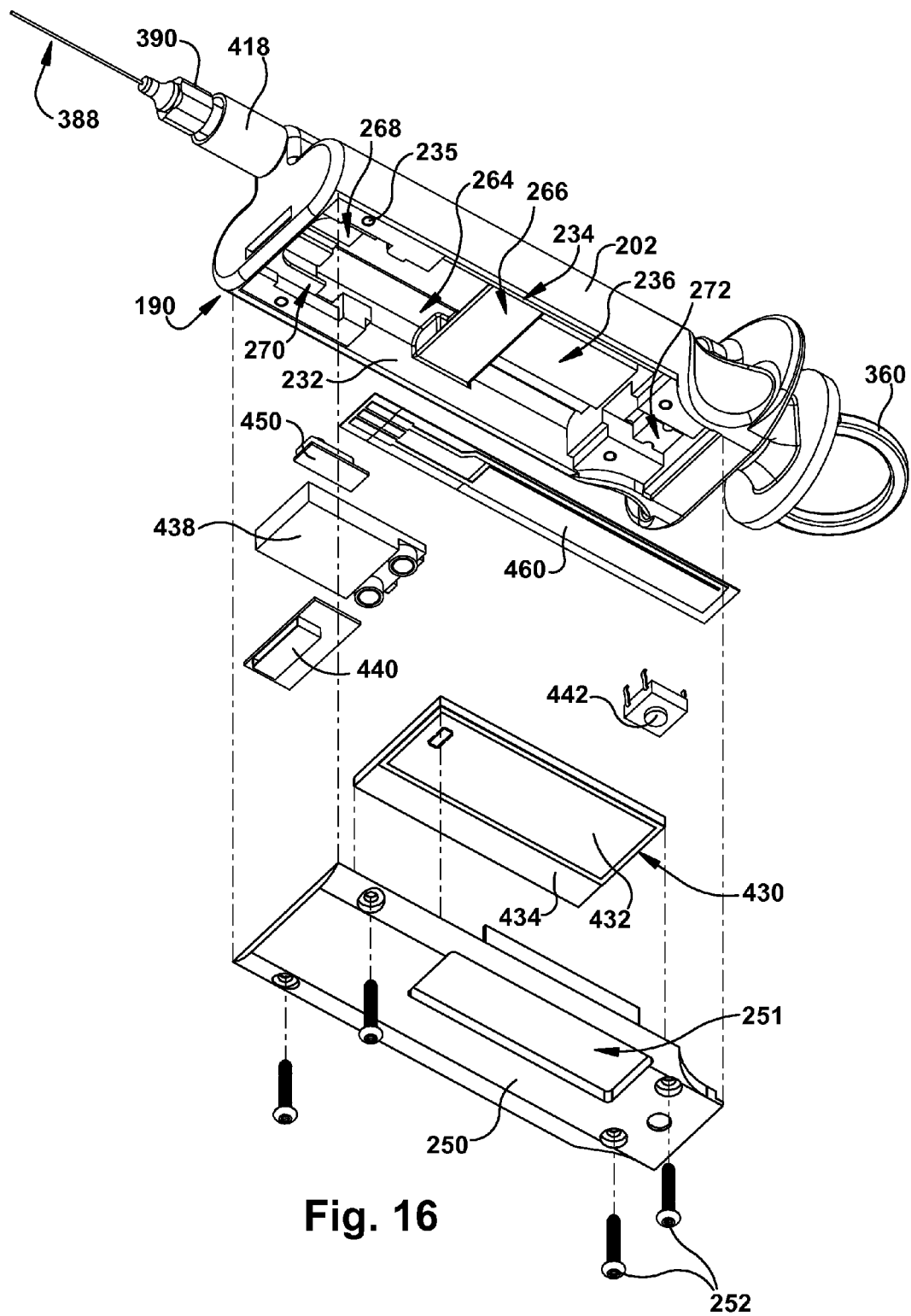
FIG. 16 is an exploded assembly view of the lacrimal drainage manometer of FIG. 7 with the cover removed and electrical components visible.

Referring to FIG. 16, the user feedback unit 430 is configured to provide user feedback based on data from the pressure sensor 450 and/or the position sensor 460. The user feedback unit 430 includes an integrated display 432 configured to provide an analog, digital, graphical and/or aural indication of sensor data. For example, the display 432 can comprise a screen disposed on, or integrated into, a first side 434 of the user feedback unit 430 facing away from the housing 200. The display 432 can be configured to provide a user with substantially real-time sensor data (e.g., pressure, flow rate and/or nasolacrimal resistance) during operation of the lacrimal drainage manometer 190.

The display 432 can provide a visible readable output of pressure (e.g., 5 mmHg) and flow rate (e.g., 400 sec/ml). It will be appreciated that the display 432 can also include additional features, such as an alarm that audibly or visibly indicates when a safety threshold (e.g., application of excessive pressure during injection) is at risk of being breached during operation of the lacrimal drainage manometer 190. In any case, the display 432 is received in the recess 266 in the housing body 202 and readable through an opening 251 in the cover 250.

The user feedback unit 430 is electrically connected to a power supply 438 and/or power saving unit (not shown) as well as a push button 442 for selectively powering the lacrimal drainage manometer 190. The power supply 438 can include a small, high performance battery shaped and dimensioned for fitting into the recess 268 in the housing body 202. The push button 442 is received in the recess 272 in the housing body 202. The power supply 438 and/or power saving unit can include a mechanism for cutting and restoring power in order to save power when the lacrimal drainage manometer 190 is not in use. For example, the power saving unit can cut power when the push button 442 has not been pressed for a certain amount of time. The power saving unit can restore power when the push button 442 is pressed.

The user feedback unit 430 is in electrical communication with each of the pressure sensor(s) 450 and the position sensor 460. For example, the user feedback unit 430 can include a digital processor circuit (not shown) that can be in electrical communication with each of the pressure sensor(s) 450 and the position sensor 460. The digital processor circuit can be held in the housing 200 with the aforementioned electrical components. The digital processor circuit can communicate (e.g., wirelessly) with the pressure sensor(s) 450 and/or the position sensor 460 to obtain desired sensor data. The wireless communication between electronic components of the present invention can be carried out, for example, using BLUETOOTH transmission configuration or any other suitable digital communication protocol or configuration.

The digital processor circuit and/or the user feedback unit 430 can cooperate with an output connection, such as a USB connection 440 received in the recess 270 in the housing body 202, to allow access to data acquired and stored in the lacrimal drainage manometer 190 related to fluid pressure, fluid flow rate, etc. The connection 440 may also allow for modifications to the circuitry's program without having to open the entire assembly, and also serves as a charging port for the rechargeable battery 438 powering the lacrimal drainage manometer 190.

The user feedback unit 430 can include hardware and/or software configured to:

read a signal from a pressure sensor 450 representative of the fluid pressure in the syringe 290;

convert the signal representative of fluid pressure in the syringe to a pressure value representative of the fluid pressure;

read signals from a position sensor 460 representative of the change in position of the plunger arm 380 corresponding to the change in position of the plunger 370 of the syringe 290;

convert the signals representative of plunger arm positions to position values representative of plunger arm positions;

calculate the fluid flow rate value through the syringe based upon the position values;

calculate an experienced nasolacrimal resistance to the expelled fluid flow as the quotient between the pressure and the fluid flow; and present the resistance value, the pressure, the syringe position, and/or the flow rate on the display 432.

As noted above, the software and/or hardware of the user feedback unit 430 is configured to calculate a resistance experienced by the syringe 290 when expelling its contents. For example, nasolacrimal resistance can be calculated from flow and pressure data by the aid of the Poiseuille-Hagen equation, or other fluid mechanics equations, which have been incorporated into the software of the user feedback unit 430. The results are visualized on the display 432, and the user can use them to make a decision on further actions.

Figure 17:
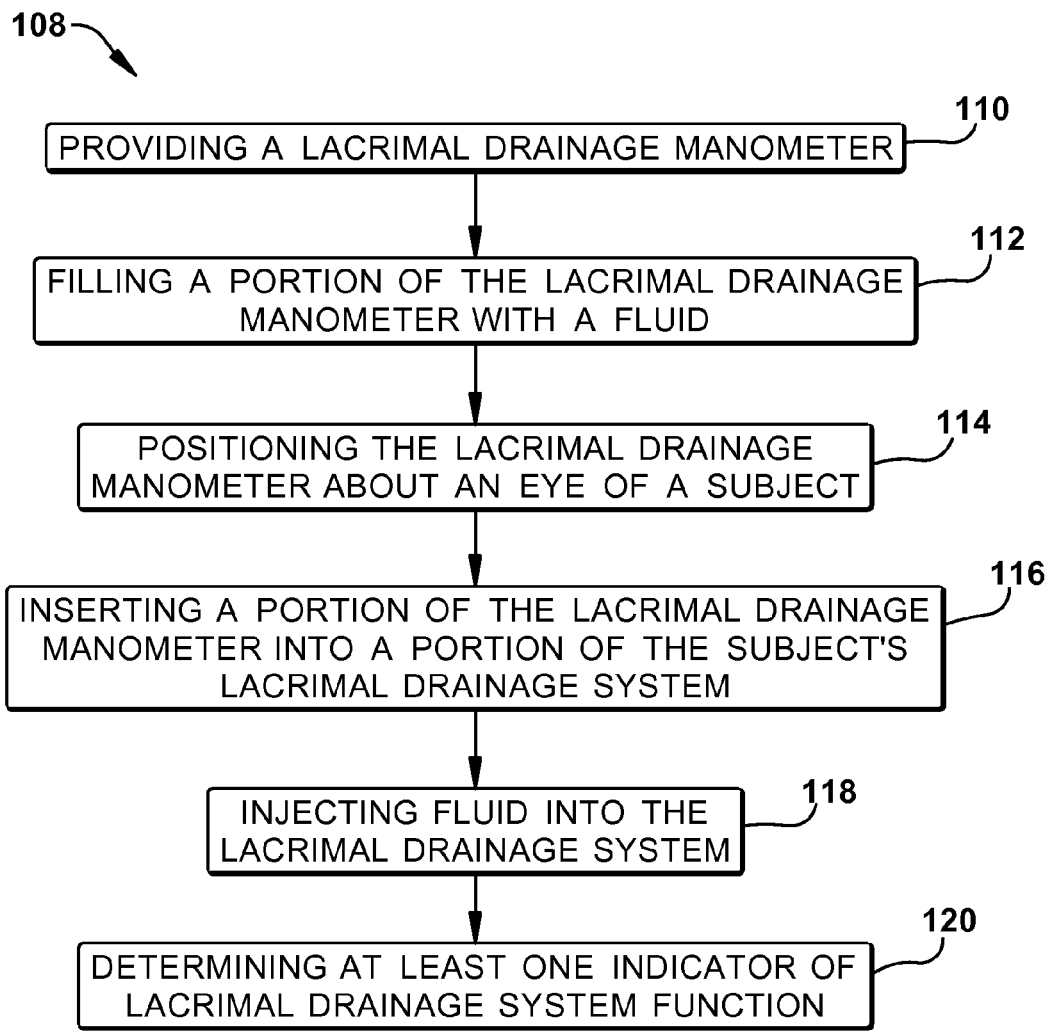
FIG. 17 is a process flow diagram illustrating a method for accurately determining at least one indicator of lacrimal drainage system function during nasolacrimal irrigation according to another aspect of the present invention.

FIG. 17 illustrates another aspect of the present invention comprising a method 108 for accurately determining at least one indicator of lacrimal drainage system function during nasolacrimal irrigation. The method 108 can be employed using either the lacrimal drainage manometer 10 of FIGS. 1A-1B or the lacrimal drainage manometer 190 of FIGS. 7-9. As described below, the method 108 advantageously provides indicators of lacrimal drainage system function (e.g., pressure readings) during nasolacrimal irrigation, which in turn provide(s) a quantitative measurement for assessing nasolacrimal patency. Determining quantitative measurements of lacrimal drainage system function during nasolacrimal irrigation provides medical practitioners useful information, which can be used to inform subsequent clinical decisions (e.g., quantifying nasolacrimal duct obstruction, guiding the choice of surgical procedure, and determining the success of lacrimal drainage procedure) and/or as an adjunct to tearing evaluation (e.g., in subjects with epiphora).

One step of the method 108 includes providing a lacrimal drainage manometer 10, 190 (Step 110). The lacrimal drainage manometer can be identically or similarly constructed as the lacrimal drainage manometer 10 shown in FIGS. 1A-B and described above or the lacrimal drainage manometer 190 shown in FIGS. 7-9 and described above. For example, the lacrimal drainage manometer 10, 190 can comprise 1) a syringe 34, 290, 2) at least one pressure sensor 36, 450 operably coupled to the syringe, 3) at least one flow sensor 38 (in the case of the lacrimal drainage manometer 10) or a position sensor 460 (in the case of the lacrimal drainage manometer 190) operably coupled to the syringe, and 4) a user feedback unit 40, 430 in electrical communication with each of the pressure sensor(s) and the flow sensor(s) or position sensor. As described above, the user feedback unit 40, 430 includes an integrated display 104, 432 configured to provide measured pressure, flow rate, and/or nasolacrimal resistance values during use of the lacrimal drainage manometer 10, 190.

If it has not been done so already, the fluid cavity 56, 312 of the syringe 34, 290 can be filled with a desired volume of a fluid (e.g., sterile saline) at Step 112. To do so, a user can first use tactile force to completely depress the piston 44, 370 within the fluid cavity 56, 312. A distal tip 122, 408 of the cannula 62, 388 can then be immersed in a volume of the fluid. Next, the piston 44, 370 can be withdrawn (i.e., towards the user) to cause the fluid to flow into the fluid cavity 56, 312. The piston 44, 370 can be continuously withdrawn until a desired volume of the fluid fills the fluid cavity 56, 312.

After filling the fluid cavity 56, 312 with a desired volume of fluid, the lacrimal drainage manometer 10, 190 is positioned about the eye 22 (e.g., the inner eye) of the subject (Step 114). For example, the cannula 62, 388 can be positioned adjacent the inferior punctum 16. It will be appreciated that the intended insertion route (e.g., inferior punctum 16 or superior punctum 14) of the cannula 62, 388 into the lacrimal drainage system 12 will depend upon the discretion of the user.

Figure 18:
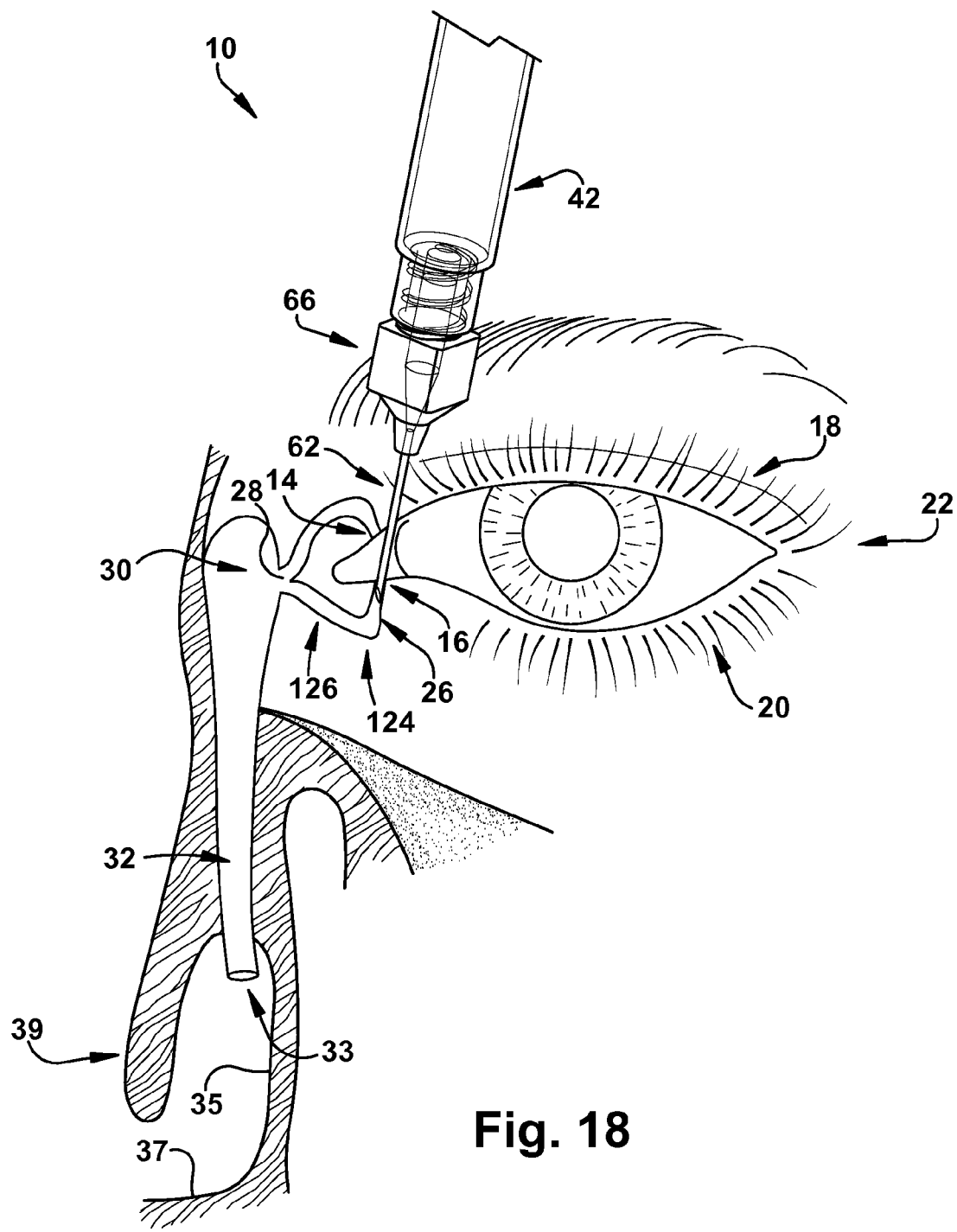
FIG. 18 is a schematic illustration showing a cannula of the lacrimal drainage manometer in FIGS. 1A-B inserted into an inferior punctum of the subject.
Figures 19, 20:
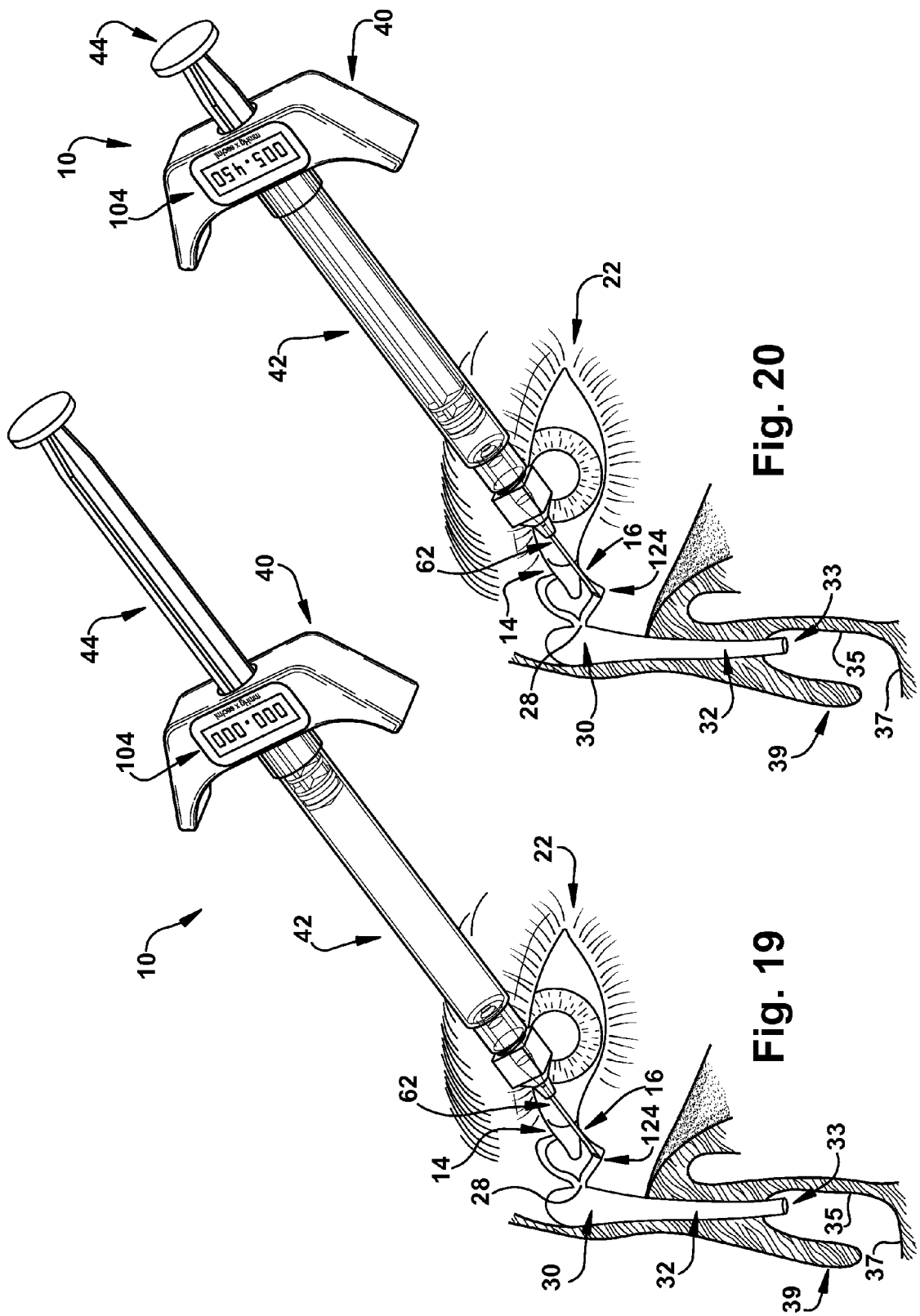
FIG. 19 is a schematic illustration showing the cannula in FIG. 18 advanced into the inferior canaliculus.
FIG. 20 is a schematic illustration showing operation of the lacrimal drainage manometer in FIG. 19.

At Step 116, a portion of the cannula 62, 388 is inserted into the lacrimal drainage system 12. As shown in FIG. 18, for example, the distal tip 122, 408 of the cannula 62, 388 is inserted into the inferior punctum 16. If needed, one or both of the puncta 14 and 16 can be dilated with a dilator (not shown) prior to insertion of the cannula 62, 388. The distal tip 122, 408 of the cannula 62, 388 can remain essentially where it is inserted or, alternatively, be progressively advanced through the inferior punctum 16 to a desired location. For example, the distal tip 122, 408 of the cannula 62, 388 can be advanced to the inferior ampulla 124 (FIG. 19). Alternatively, the distal tip 122, 408 can be further advanced past the inferior ampulla 124 into a portion of the inferior horizontal canaliculus 126. It will be appreciated that the distal tip 122, 408 of the cannula 62, 388 can be advanced to other locations within the lacrimal drainage system 12, such as the valve of Rosenmüller (not shown) or the lacrimal sac 30.

Once the distal tip 122, 408 of the cannula 62, 388 is appropriately positioned within the lacrimal drainage system 12, the user can apply tactile force to the handle portion 80, 360 of the piston 44, 350 (Step 118). As force is applied to the piston 44, 350, fluid is flowed from the fluid cavity 56, 312, through the lumen 76, 402 of the detachable member 66, 390, and out of the cannula 62, 388 into the lacrimal drainage system 12. During application of force to the piston 44, 350, the pressure sensor 36, 450 provides a signal representative of fluid pressure inside the fluid cavity 56, 312 to the user feedback unit 40, 430 (Step 120). As shown in FIG. 20, for example, the pressure signal can be provided to the digital processor circuit, which then visually displays the pressure (e.g., in mmHg) on the display 104, 432.

As described above, in the case of the lacrimal drainage manometer 10, the flow sensor 38 may also provide a signal representative of fluid flow (e.g., in sec/ml) through the syringe 34 to the user feedback unit 40. In the case of the lacrimal drainage manometer 190, the position sensor 460 may also provide a signal representative of the change in position of the plunger arm 380 and, thus, a signal indicative of the change in position of the piston 370 that is used to calculate the fluid flow rate through the syringe 290. This fluid flow rate is provided to the user feedback unit 430. In both cases, based on the visualized sensor data, the user can inform his or her decision as to the appropriate course of action. As explained below, for example, the method 108 can be used to determine the presence of an obstruction in the lacrimal drainage system 12.

To determine the presence of an obstruction in the lacrimal drainage system 12, Steps 110-120 can be performed as described above. At Step 120, the determination of at least one indicator of lacrimal drainage system function may also be performed while assessing the lacrimal drainage system 12 using tactile sensation. As described above, the detected pressure, fluid flow rate, and/or nasolacrimal resistance can be visually displayed on the display 104, 432 of the user feedback unit 40, 430.

After determining the level of the at least one indicator of lacrimal drainage system function, the determined level can be compared to a normal or control level. One skilled in the art will appreciate how to determine a normal or control level. For example, the normal or control level may be determined by having previously determined a healthy baseline value of the at least one indicator for a given subject, by averaging normal or baseline levels from a number of healthy subjects, or by referring to a known or validated source of normal or control values (e.g., a medical journal or database).

An increased or decreased level of the at least one indicator (as compared to the control level) can indicate that there is an obstruction in the lacrimal drainage system 12. For example, an increased nasolacrimal resistance and/or pressure level can indicate the presence of an obstruction. Alternatively, a decreased fluid flow rate can indicate the presence of an obstruction. It will be appreciated that an obstruction can be functional or physical. A physical obstruction, for example, can include stenosis, a foreign body, or some other blockage in the lacrimal drainage system 12. Sometimes, the lacrimal drainage system 12 may appear patent by determining normal pressure, flow rate and/or resistance values; however, there may be a functional obstruction, such as collapse of all or part of the lacrimal pathway (e.g., the lacrimal sac 30). Thus, the present invention may be used to determine the nature and position of an obstruction within the lacrimal drainage system 12.

The following example is for the purpose of illustration only and is not intended to limit the scope of the claims, which are appended hereto.

EXAMPLE

Methods

We performed a prospective review of case series. Data was collected on age of patient, gender, duration of symptoms, previous treatments, dye disappearance testing results, percentage of irrigation through the nasolacrimal duct, eyelid laxity, presence of ectropion, and the various pressure measurements.

We quantitatively measured the pressure generated during manual, conventional probing and irrigation using a standard 3 cc syringe, and experimental probing and irrigation using an infusion pump (Medfusion 2010 Infusion Pump, MEDEX Inc., Carlsbad, Calif.) to deliver a constant flow rate of saline. We measured the steady state irrigation pressure using a disposable in-line pressure transducer with integrated pressure sensor (BIOTRANS Disposable Pressure Measuring System, BIOSENSORS International, Newport Beach, Calif.) and digital pressure monitor (EAGLE 3000 patient monitor, MARQUETTE ELECTRONICS, Milwaukee, Wis.). Resistance was calculated from the known flow rate and pressure measurements. We compared pressure generated and resistance between patients with lacrimal drainage obstruction and control patients with no obstruction as determined by clinical exam and dye disappearance testing.

Results

During conventional testing, manual pressure was estimated to deliver 1 cc of saline over an average of 30 seconds for a flow rate of 0.033 milliliters per second. During experimental testing, the syringe pump delivered saline over a flow rate of 0.028 milliliters per second (a known rate of 100 milliliters per hour). Seventeen patients (3 non-obstructive, 14 obstructive) underwent bilateral testing via both conventional probing and irrigation and experimental probing and irrigation via a syringe pump delivery system. The average age was 62.7 years (range, 19 to 95 years).

The average pressure for conventional non-obstructive patients was 101.6 mmHg (range, 46 to 200 mmHg) and calculated resistance was 3078 mmHg×sec/ml. The average pressure for experimental non-obstructive patients was 77.7 mmHg (range, 12 to 209 mmHg) and calculated resistance was 2775 mmHg×sec/ml.

The average pressure for conventional partially obstructed patients was 145.5 mmHg (range, 30 to 300) and calculated resistance was 4409 mmHg×sec/ml. The average pressure for experimental partially obstructed patients was 86.1 mmHg (range, 22 to 266 mmHg) and calculated resistance was 3071 mmHg×sec/ml.

The average pressure for conventional completely obstructed patients was 147.4 mmHg (range, 71 to 242 mmHg) and calculated resistance was 4467 mmHg×sec/ml. The average pressure for experimental completely obstructed patients was 91.9 mmHg (range, 36 to 186 mmHg) and calculated resistance was 3282 mmHg×sec/ml.

From the above description of the invention, those skilled in the art will perceive improvements, changes and modifications. For example, it will be appreciated that detachable member 66, 390 may be an integral part of the syringe body 42, 300 such that the detachable member is not separable from the syringe body. Such improvements, changes, and modifications are within the skill of the art and are intended to be covered by the appended claims.

Having described the invention, the following is claimed:

1. A lacrimal drainage manometer comprising:
   a syringe including a syringe body, a piston, and a plunger arm connected with and having a centerline extending parallel to the piston, the syringe body defining a fluid cavity in fluid communication with a cannula configured for insertion into at least a portion of a lacrimal drainage system, the piston for dispensing a fluid from the fluid cavity through the cannula;
   a pressure sensor operably coupled to the syringe for measuring fluid pressure in the fluid cavity;
   a position sensor operably coupled to the syringe and extending parallel to the length of the plunger arm for measuring the position of the plunger arm to indirectly measure the position of the piston relative to the syringe body; and
   a user feedback unit in electrical communication with the pressure sensor and the position sensor for providing user feedback based on data from at least one of the pressure sensor and the position sensor indicative of a condition of the lacrimal drainage system.

2. The lacrimal drainage manometer of claim 1, wherein the position sensor comprises a linear resistor that monitors the change in position of the plunger arm and outputs a signal indicative of the change in position.

3. The lacrimal drainage manometer of claim 2, wherein the user feedback unit includes a controller that receives the position signal from the position sensor and determines a flow rate of the fluid into the lacrimal drainage system based upon the position signal.

4. The lacrimal drainage manometer of claim 1 further comprising a housing through which the syringe extends, the pressure sensor being mounted in a passage of the housing in fluid communication with the fluid cavity.

5. The lacrimal drainage manometer of claim 1, wherein the pressure sensor is mounted on a distal surface of the piston.

6. The lacrimal drainage manometer of claim 1, wherein the cannula is integrally formed with a detachable member configured to mate with the syringe body, the detachable member having a lumen extending therethrough, the lumen being in fluid communication with the fluid cavity and the cannula.

7. The lacrimal drainage manometer of claim 1, wherein the user feedback unit comprises a housing having an integrated display for providing the data to a user.

8. The lacrimal drainage manometer of claim 7, wherein the housing has an ergonomic, wing-shaped configuration.

9. The lacrimal drainage manometer of claim 7, wherein the syringe body extends through at least a portion of the housing.

10. The lacrimal drainage manometer of claim 7, wherein the housing is configured to releasably engage the syringe body.

11. The lacrimal drainage manometer of claim 7, wherein the housing is serially reusable with different syringes and a respective syringe is single-use disposable.

12. A method for accurately determining at least one indicator of lacrimal drainage system function during nasolacrimal irrigation, the method comprising the steps of:
providing a lacrimal drainage manometer comprising a syringe in fluid communication with a cannula, a pressure sensor operably coupled to the syringe for determining fluid pressure within the syringe, a position sensor operably coupled to the syringe for determining fluid flow rate through the syringe based upon the change in position of a portion of the syringe, and a user feedback unit in electrical communication with each of the pressure sensor and the position sensor;
inserting a portion of the cannula into a portion of the lacrimal drainage system; and
quantitatively determining at least one indicator of lacrimal drainage system function during injection of a fluid through the cannula, the at least one indicator being at least one of nasolacrimal drainage pressure, fluid flow rate or nasolacrimal resistance.

13. The method of claim 12, wherein the portion of the lacrimal drainage system includes an inferior punctum and/or a superior punctum.

14. The method of claim 12, wherein the portion of the lacrimal drainage system includes an inferior canaliculus and/or superior canaliculus.

15. The method of claim 12, wherein the step of quantitatively determining at least one indicator of lacrimal drainage system function further comprises the step of reading the detected at least one indicator on the user feedback unit.

16. A method for determining the presence of an obstruction in a lacrimal drainage system, the method comprising the steps of:
providing a lacrimal drainage manometer comprising a syringe in fluid communication with a cannula, a pressure sensor operably coupled to the syringe for determining fluid pressure within the syringe, a position sensor operably coupled to the syringe for determining fluid flow rate through the syringe, and a user feedback unit in electrical communication with each of the pressure sensor and the position sensor;
inserting a portion of the cannula into a portion of the lacrimal drainage system; and
quantitatively determining at least one indicator of lacrimal drainage system function during injection of a fluid through the cannula, the at least one indicator being at least one of lacrimal drainage pressure, fluid flow or nasolacrimal resistance;
wherein an increased or decreased level of the at least one indicator as compared to a control level is indicative of an obstruction.

17. The method of claim 16 further comprising measuring the change in position of a piston of the syringe with the position sensor to determine the fluid pressure within the syringe.

18. The method of claim 16, wherein the obstruction is a physical obstruction.

19. The method of claim 16, wherein the obstruction is a functional obstruction.

20. The method of claim 16, wherein the portion of the lacrimal drainage system includes an inferior punctum and/or a superior punctum.

21. The method of claim 16, wherein the portion of the lacrimal drainage system includes an inferior canaliculus and/or superior canaliculus.

22. The method of claim 16, wherein the step of quantitatively determining at least one indicator of lacrimal drainage system function further comprising the step of reading the detected at least one indicator on the user feedback unit.

23. The lacrimal drainage manometer of claim 1, wherein the piston is spaced from the plunger arm.

24. The lacrimal drainage manometer of claim 1, wherein the plunger arm is positioned outside the fluid cavity.

* * * * *